United States Patent [19]
Conkling et al.

[11] Patent Number: 5,750,386
[45] Date of Patent: May 12, 1998

[54] PATHOGEN-RESISTANT TRANSGENIC PLANTS

[75] Inventors: Mark A. Conkling, Fuquay-Varina; Charles H. Opperman; Christopher G. Taylor, both of Raleigh, all of N.C.

[73] Assignee: North Carolina State University, Raleigh, N.C.

[21] Appl. No.: 558,865

[22] Filed: Nov. 15, 1995

Related U.S. Application Data

[63] Continuation of Ser. No. 236,678, May 2, 1994, abandoned, which is a continuation of Ser. No. 770,082, Oct. 4, 1991, abandoned.

[51] Int. Cl.$^6$ .......................... C12N 15/00; C12N 15/63; C12N 15/82; A01H 5/00
[52] U.S. Cl. ............. 435/172.3; 800/205; 800/DIG. 9; 800/DIG. 23; 800/DIG. 26; 800/DIG. 27; 800/DIG. 42; 800/DIG. 43; 800/DIG. 54; 435/172.1; 435/320.1; 536/24.1; 47/58
[58] Field of Search ................... 800/205, DIG. 23, 800/26, 27, 42, 54, DIG. 9, DIG. 43, DIG. 52; 435/172.3, 320.1, 172.1; 536/24.1, 23.6; 935/6, 35, 36, 43; 47/58; 514/44

[56] References Cited

U.S. PATENT DOCUMENTS

| | | | |
|---|---|---|---|
| 4,940,840 | 7/1990 | Suslow et al. | 800/205 |
| 4,948,734 | 8/1990 | Edwards et al. | 435/252.5 |
| 5,015,580 | 5/1991 | Christou et al. | 435/172.3 |
| 5,034,323 | 7/1991 | Jorgensen et al. | 435/172.3 |
| 5,093,120 | 3/1992 | Edwards et al. | 424/93 |
| 5,589,622 | 12/1996 | Gurr et al. | 800/205 |
| 5,597,945 | 1/1997 | Jaynes et al. | 800/205 |
| 5,597,946 | 1/1997 | Jaynes et al. | 800/205 |

FOREIGN PATENT DOCUMENTS

| | | |
|---|---|---|
| 0 285 361 A3 | 3/1988 | European Pat. Off. . |
| 0 298 918 | 1/1989 | European Pat. Off. . |
| 0307841 | 3/1989 | European Pat. Off. ........ C12N 15/00 |
| 0 375 091 A1 | 12/1989 | European Pat. Off. . |
| 0 425 004 A3 | 10/1990 | European Pat. Off. . |
| 0 427 529 A1 | 11/1990 | European Pat. Off. . |
| 0 479 180 A3 | 9/1991 | European Pat. Off. . |
| 42 04 103 A1 | 2/1992 | Germany . |
| 8900194 | 1/1989 | WIPO . |
| 8900194 | 6/1989 | WIPO .............. C12N 1/06 |
| WO 90/07936 | 7/1990 | WIPO . |
| WO 91/13992 | 4/1991 | WIPO . |
| WO 91/13994 | 9/1991 | WIPO . |
| WO 92/04453 | 3/1992 | WIPO . |
| WO 92/21757 | 12/1992 | WIPO . |
| WO 93/10251 | 5/1993 | WIPO .............. C12N 15/82 |
| WO 93/18170 | 9/1993 | WIPO . |
| WO 93/19188 | 9/1993 | WIPO . |

OTHER PUBLICATIONS

W. Jun; Preparation of transgenic plants for control of virosis, *Chem. Abstracts* 113, No. 15, Abstract No. 127723, 1990.

M. Conkling et al., *Plant Physiol.* 93, 1203–1211 (1990).
S. Gurr et al., *Mol. Gen. Genet.* 226, 361–366 (1991).
R. Hartley, *J. Mol. Biol.* 202, 913–915 (1988).
C. Operman et al., *Plant Disease* 72, No. 10, 869–871 (1988).
C. Paddon et al., *Journal of Bacteriology* 171, No. 2, 1185–1187 (1989).
C. Paddon and R. Hartley, *Gene* 40, 231–239 (1986).
Y. Yamamoto et al., *J. Cell. Biochem.* 13D (Supp.), 313 (1989).
C. Mariani et al., *Nature* 347, 737–741 (1990).
Delauney et al.; A Stable Bifunctional Antisense Transcript Inhibiting Gene Expression in Transgenic Plants, *Proc. Nat'l. Acad. Sci. USA* 85:4300–4304 (1988).
de Waele; Potential of Plant Genetic Engineering for Nematode Control (Abstract), *Phytophylactica* 23(2):182 (1991).
Gurr et al.; Identification of Plant Genes Expressed at the Feeding Site of the Potato Cyst Nematode, *J. Cell. Biochem.* Supp 15A:56 (1991).
Hammond–Kosack et al.; changes in Abundance of Translatabale mRNA Species in Potato Roots and Leaves Following root Invasion by Cyst–Nematode G. Rostochiensis Pathotypes, *Phys. Mol. Plant. Pathol.* 37:339–354 (1990).
Haseloff and Gerlach, Simple RNA Enzymes with New and Highly Specific Endoribonuclease Activities, *Nature* 334:585 (1988).
Perlak et al.; Modification of the Coding Sequence Enhances Plant Expression of Insect Control Protein Genes, *Proc. Nat'l. Acad. Sci. USA* 88:3324–3328 (1991).
Potrykus; Gene Transfer to Plants: Assessment of Published Approaches and Results, *Annu. Rev. Plant Physiol. Plant Mol. Biol.* 42:205–225 (1991).
Rice et al.; Changes in Cell Structure in Roots of Resistant Potatoes Parasitized by Potato Cyst Nematodes. 2. Potatoes With Resistance Derived from Solanum Vernei, *Physiol. Mol. Plant Pathol.* 31:1–14 (1987).
Tomes et al.; Transgenic Tobacco Plants and Their Progeny Derived by Mocroprojectile Bombardment of Tobacco Leaves, *Plant Mol. Biol.* 31:216–268 (1990).
Vandekerckhove et al.; Enkephalins Produced in Transgenic Plants Using Modified 2S Seed Storage Proteins. *Bio/Technology* 7:929–932 (1989).

(List continued on next page.)

*Primary Examiner*—Charles C. P. Rories
*Attorney, Agent, or Firm*—Myers, Bigel, Sibley & Sajovec, L.L.P.

[57] ABSTRACT

Recombinant pathogen-resistant plants comprise transformed plant cells, with the transformed plant cells containing a heterologous DNA construct comprising an expression cassette. The construct comprises a promoter, a structural gene positioned downstream from the promoter, and a termination sequence such as the nos terminator positioned downstream from the structural gene. The promoter is one which is activated by a plant pathogen which attacks the plant, such as the RB7 nematode-responsive element. The structural gene encodes a product such as Barnase which is toxic to the plant cells.

46 Claims, 2 Drawing Sheets

OTHER PUBLICATIONS

Yamamoto et al.; Root–Specific Genes from Tobacco and Arabidopsis Homologous to an Evolutionarily Conserved Gene Family of Membrane Channel Proteins, *Nucl. Acids. Res.* 18(24):7449 (1990).

Yamamoto et al.; Characterization of cis–Acting Sequences Regulating Root–Specific Gene Expression in Tobacco, *The Plant Cell* 3:371–382 (1991).

T. Maniatis et al. Science, vol. 236, (5 Jun. '87) pp. 1237–1244.

M.G.K. Jones, et al. Annals of Applied Biology (1981) vol. 97, pp. 353–372.

A. Niebel et al. (Abstract) J. Cell Biochem., Suppl. O, vol. 13, Pt. D (1989) p. 323.

M. Chapekar et al. BBRC, vol. 151 (1988) pp. 1180–1187.

R. Hartley J. Mol. Biology, vol. 202 (1988) pp. 913–915.

W. Gordon–Kamm et al. The Plant Cell, vol. 2 (1990) pp. 603–618.

Shaw, P., et al. Cell, vol. 40 (1985) pp. 907–912.

Takahashi, K., et al. Nature, vol. 319 (1986) pp. 121–126.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 3426 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Nicotiana tabacum ( v i i ) IMMEDIATE SOURCE:
        ( B ) CLONE: TobRB7-5A ( i x ) FEATURE:
        ( A ) NAME/KEY: promoter
        ( B ) LOCATION: 1..1877

( i x ) FEATURE:
        ( A ) NAME/KEY: CDS
        ( B ) LOCATION: join(1954..2079, 2376..2627, 2913..3284)

( i x ) FEATURE:
        ( A ) NAME/KEY: 5'UTR
        ( B ) LOCATION: 1878..1953

( x i ) SEQUENCE DESCRIPTION: SEQ ID NO:1:

```
GGATCCCCCT  CTTTTATAAT  AGAGGGTCAT  TACTTTATTT  ACAATAAAAT  AATAAAATAA      60
AGCATATAGT  GGAGGACCCA  TGATGACTTG  TTTCTTCCTC  GATTTTCGCC  GAGATTCTCT     120
CCCATAGTGC  GGTTGCAACG  GCCCTTGTCT  GCGAGCTCGA  TACTGGTTCG  AGCTCGGCAT     180
TGGACCGAGC  CCTCGACCTT  GGTCCGAGCT  CGATTCTGAC  TTGGGGTCTC  GGTATTCGGG     240
GTGAGTGTTG  GTCGGTCTAT  GCATCTTCGA  TAATCTCCGT  TTTGCCTCGT  AGTTCGATTT     300
GGATATGAGC  TCGATAATGA  TACCGAGCTT  GTCATTGATC  GGTCTTAGAG  CTCGAAGTTC     360
GACGCCTTTA  CTTCGGACCT  TGACCGAGCT  TGTTATGTAG  ATATCCTTTG  ATCGAAACAT     420
TATCGTTTTG  ACCAATCCGT  ACGACTGACT  CAAATCGATT  TGACCGCACA  CAAGATTATT     480
TTCGAAAGAC  CCTCGACGTC  TTGGAGTATA  AATAATTTA   GTAAGAGAG   TAATTGTTCG     540
TTAAAAATCT  TGACACCATT  CCAAGCATAC  CCCTTATTGT  ACTTCAATTA  ATTATCATTA     600
TATCAGCATA  AACATTATAA  TAAGTTTCTT  GCGTGTTGGA  ACGTCATTTT  AGTTATTCTA     660
AAGAGGAAAT  AGTTTCTTTT  TTGCTCATGA  CATCAGACAT  CTGGACTACT  ATACTGGAGT     720
TTACCTTTTC  TTCTCCTCTT  TTTCTTATTG  TTCCTCTAAA  AAAAATTATC  ACTTTTTAAA     780
TGCATTAGTT  AAACTTATCT  CAACAACGTT  TAAAATTCAT  TTCTTGAATG  CCCATTACAA     840
TGTAATAGTA  TAACTTAATT  AGTCGTCTCC  ATGAACCATT  AATACGTACG  GAGTAATATA     900
AAACACCATT  GGGGAGTTCA  ATTTGCAATA  ATTTCTTGCA  AAAATGTAAA  GTACCTTTTT     960
GTTCTTGCAA  AATTTTACAA  ATAAAAATTT  GCAGCTCTTT  TTTTTCTCTC  TCTCCAAATA    1020
CTAGCTCAAA  ACCCACAAAT  ATTTTGAAT   TTATGGCATA  CTTTAGAAT   GCGTTTGATG    1080
```

| | |
|---|---|
| CAACTATTTT CCTTTAGGAA ATATTCACAA CAATCTAAGA CAATCAAAAA GTAGAAAATA | 1140 |
| GTTTGTAAAA AGGGATGTGG AGGACATCTT AATCAAATAT TTCAGTTTA AAACTTGAAA | 1200 |
| ATGAAAAAAC ACCCGAAAGG AAATGATTCG TTCTTTAATA TGTCCTACAC AATGTGAATT | 1260 |
| TGAATTAGTT TGGTCATACG GTATATCATA TGATTATAAA TAAAAAAAAT TAGCAAAAGA | 1320 |
| ATATAATTTA TTAAATATTT TACACCATAC CAAACACAAC CGCATTATAT ATAATCTTAA | 1380 |
| TTATCATTAT CACCAGCATC AACATTATAA TGATTCCCCT ATGCGTTGGA ACGTCATTAT | 1440 |
| AGTTATTCTA AACAAGAAAG AAATTGTTC TTGACATCAG ACATCTAGTA TTATAACTCT | 1500 |
| AGTGGAGCTT ACCTTTCTT TTCCTTCTTT TTTTCTTCT TAAAAAAATT ATCACTTTTT | 1560 |
| AAATCTTGTA TATTAGTTAA GCTTATCTAA ACAAAGTTTT AAATTCATTT CTTAAACGTC | 1620 |
| CATTACAATG TAATATAACT TAGTCGTCTC AATTAAACCA TTAATGTGAA ATATAAATCA | 1680 |
| AAAAAAGCCA AAGGGCGGTG GGACGGCGCC AATCATTTGT CCTAGTCCAC TCAAATAAGG | 1740 |
| CCCATGGTCG GCAAAACCAA ACACAAAATG TGTTATTTTT AATTTTTCC TCTTTTATTG | 1800 |
| TTAAAGTTGC AAAATGTGTT ATTTTTGGTA AGACCCTATG GATATATAAA GACAGGTTAT | 1860 |
| GTGAAACTTG GAAAACCATC AAGTTTTAAG CAAAACCCTC TTAAGAACTT AAATTGAGCT | 1920 |
| TCTTTTGGGG CATTTTCTA GTGAGAACTA AAA ATG GTG AGG ATT GCC TTT GGT | 1974 |
|  Met Val Arg Ile Ala Phe Gly |  |
|  1       5 |  |
| AGC ATT GGT GAC TCT TTT AGT GTT GGA TCA TTG AAG GCC TAT GTA GCT | 2022 |
| Ser Ile Gly Asp Ser Phe Ser Val Gly Ser Leu Lys Ala Tyr Val Ala |  |
|     10          15          20 |  |
| GAG TTT ATT GCT ACT CTT CTC TTT GTG TTT GCT GGG GTT GGG TCT GCT | 2070 |
| Glu Phe Ile Ala Thr Leu Leu Phe Val Phe Ala Gly Val Gly Ser Ala |  |
|  25          30          35 |  |
| ATA GCT TAT AGTAAGTAAC ACTTCTCTAA TTAAACTTGC ATGCTAACAT | 2119 |
| Ile Ala Tyr |  |
|  40 |  |
| AAATACTTAA TCTGCTCTAG CACTAAATAG TAAAAAGAGC AATCAGGTGC ACTAAGGTCC | 2179 |
| CATTAATTCG TTATGCACAT GCCACGGAGT CTAGAGAAAG ACTAGACTGG CTCTATCATA | 2239 |
| TTCAATTTTA CCTTACATTT TACTAGATGC CGTTTTCTCA ATCCATAACC GAAAACAACA | 2299 |
| TAACTTTTAC AGTTACACCA AGACTGCCTA ATTAACCTTT TTTTTTTTT TTTTGCTTT | 2359 |
| GTGGGGTGAT TTTGTA GAT AAA TTG ACA GCA GAT GCA GCT CTT GAT CCA | 2408 |
|  Asp Lys Leu Thr Ala Asp Ala Ala Leu Asp Pro |  |
|  45          50 |  |
| GCT GGT CTA GTA GCA GTA GCT GTG GCT CAT GCA TTT GCA TTG TTT GTT | 2456 |
| Ala Gly Leu Val Ala Val Ala Val Ala His Ala Phe Ala Leu Phe Val |  |
|  55          60          65 |  |
| GGG GTT TCC ATA GCA GCC AAT ATT TCA GGT GGC CAT TTG AAT CCA GCT | 2504 |
| Gly Val Ser Ile Ala Ala Asn Ile Ser Gly Gly His Leu Asn Pro Ala |  |
|  70          75          80          85 |  |
| GTA ACT TTG GGA TTG GCT GTT GGT GGA AAC ATC ACC ATC TTG ACT GGC | 2552 |
| Val Thr Leu Gly Leu Ala Val Gly Gly Asn Ile Thr Ile Leu Thr Gly |  |
|          90          95          100 |  |
| TTC TTC TAC TGG ATT GCC CAA TTG CTT GGC TCC ACA GTT GCT TGC CTC | 2600 |
| Phe Phe Tyr Trp Ile Ala Gln Leu Leu Gly Ser Thr Val Ala Cys Leu |  |
|  105          110          115 |  |
| CTC CTC AAA TAC GTT ACT AAT GGA TTG GTATGTACTG CTATCATTTT | 2647 |
| Leu Leu Lys Tyr Val Thr Asn Gly Leu |  |
|  120          125 |  |
| CAATCCATAT TATATGTCTT TTATATTTT TCACAACTTC AATAAAAAAA CAACTTTACC | 2707 |
| TAAGACCAGC CTAAGCCGTC GTATAGCCGT CCATCCAACC CTTTAAATTA AAAAGAGCCG | 2767 |

```
GCATAGTCAT AATATATGTA TATTTCATGT AGAATATTTG TATAATTAGT GTATATTGTA         2827

CGTATATCGA CTAGAAAAAA ATAAATAATG AATATGACTG TTTATTTGTA ATTGGAGTTG         2887

GGCCTCATAT GTTGGTTTTT GGCAG GCT GTT CCA ACC CAT GGA GTT GCT GCT           2939
                            Ala Val Pro Thr His Gly Val Ala Ala
                                        130                 135

GGG CTC AAT GGA TTA CAA GGA GTG GTG ATG GAG ATA ATC ATA ACC TTT           2987
Gly Leu Asn Gly Leu Gln Gly Val Val Met Glu Ile Ile Ile Thr Phe
            140             145                 150

GCA CTG GTC TAC ACT GTT TAT GCA ACA GCA GCA GAC CCT AAA AAG GGC           3035
Ala Leu Val Tyr Thr Val Tyr Ala Thr Ala Ala Asp Pro Lys Lys Gly
            155             160                 165

TCA CTT GGA ACC ATT GCA CCC ATT GCA ATT GGG TTC ATT GTT GGG GCC           3083
Ser Leu Gly Thr Ile Ala Pro Ile Ala Ile Gly Phe Ile Val Gly Ala
        170             175                 180

AAC ATT TTG GCA GCT GGT CCA TTC AGT GGT GGG TCA ATG AAC CCA GCT           3131
Asn Ile Leu Ala Ala Gly Pro Phe Ser Gly Gly Ser Met Asn Pro Ala
185                 190                 195

CGA TCA TTT GGG CCA GCT GTG GTT GCA GGA GAC TTT TCT CAA AAC TGG           3179
Arg Ser Phe Gly Pro Ala Val Val Ala Gly Asp Phe Ser Gln Asn Trp
200                 205                 210                 215

ATC TAT TGG GCC GGC CCA CTC ATT GGT GGA GGA TTA GCT GGG TTT ATT           3227
Ile Tyr Trp Ala Gly Pro Leu Ile Gly Gly Gly Leu Ala Gly Phe Ile
                220             225                 230

TAT GGA GAT GTC TTT ATT GGA TGC CAC ACC CCA CTT CCA ACC TCA GAA           3275
Tyr Gly Asp Val Phe Ile Gly Cys His Thr Pro Leu Pro Thr Ser Glu
            235             240                 245

GAC TAT GCT TAAAACTTAA AAGAAGACAA GTCTGTCTTC AATGTTCTT                    3324
Asp Tyr Ala
        250

TGTGTGTTTT CAAATGCAAT GTTGATTTTT AATTTAAGCT TGTATATTA TGCTATGCAA          3384

CAAGTTTGTT TCCAATGAAA TATCATGTTT TGGTTTCTTT TG                            3426

( 2 ) INFORMATION FOR SEQ ID NO:2:

( i ) SEQUENCE CHARACTERISTICS:
              ( A ) LENGTH: 250 amino acids
              ( B ) TYPE: amino acid
              ( D ) TOPOLOGY: linear ( i i ) MOLECULE TYPE: protein ( x i ) SEQUENCE DESCRIPTION: SEQ ID NO:2:

Met Val Arg Ile Ala Phe Gly Ser Ile Gly Asp Ser Phe Ser Val Gly
 1               5                  10                  15

Ser Leu Lys Ala Tyr Val Ala Glu Phe Ile Ala Thr Leu Leu Phe Val
            20                  25                  30

Phe Ala Gly Val Gly Ser Ala Ile Ala Tyr Asp Lys Leu Thr Ala Asp
            35                  40                  45

Ala Ala Leu Asp Pro Ala Gly Leu Val Ala Val Ala His Ala
        50                  55                  60

Phe Ala Leu Phe Val Gly Val Ser Ile Ala Ala Asn Ile Ser Gly Gly
65                  70                  75                  80

His Leu Asn Pro Ala Val Thr Leu Gly Leu Ala Val Gly Gly Asn Ile
                85                  90                  95

Thr Ile Leu Thr Gly Phe Phe Tyr Trp Ile Ala Gln Leu Leu Gly Ser
            100                 105                 110

Thr Val Ala Cys Leu Leu Leu Lys Tyr Val Thr Asn Gly Leu Ala Val
            115                 120                 125
```

| Pro | Thr<br>130 | His | Gly | Val | Ala | Ala<br>135 | Gly | Leu | Asn | Gly | Leu<br>140 | Gln | Gly | Val | Val |
|---|---|---|---|---|---|---|---|---|---|---|---|---|---|---|---|
| Met<br>145 | Glu | Ile | Ile | Ile | Thr<br>150 | Phe | Ala | Leu | Val | Tyr<br>155 | Thr | Val | Tyr | Ala | Thr<br>160 |
| Ala | Ala | Asp | Pro | Lys<br>165 | Lys | Gly | Ser | Leu | Gly<br>170 | Thr | Ile | Ala | Pro | Ile<br>175 | Ala |
| Ile | Gly | Phe | Ile<br>180 | Val | Gly | Ala | Asn | Ile<br>185 | Leu | Ala | Ala | Gly | Pro<br>190 | Phe | Ser |
| Gly | Gly | Ser<br>195 | Met | Asn | Pro | Ala | Arg<br>200 | Ser | Phe | Gly | Pro | Ala<br>205 | Val | Val | Ala |
| Gly | Asp<br>210 | Phe | Ser | Gln | Asn | Trp<br>215 | Ile | Tyr | Trp | Ala | Gly<br>220 | Pro | Leu | Ile | Gly |
| Gly<br>225 | Gly | Leu | Ala | Gly | Phe<br>230 | Ile | Tyr | Gly | Asp | Val<br>235 | Phe | Ile | Gly | Cys | His<br>240 |
| Thr | Pro | Leu | Pro | Thr<br>245 | Ser | Glu | Asp | Tyr | Ala<br>250 | | | | | | |

(2) INFORMATION FOR SEQ ID NO:3:

(i) SEQUENCE CHARACTERISTICS:
(A) LENGTH: 1933 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

```
CCCATATGAA AGACCCTCGA CGTCTTGGAG TATAAAATAA TTTAGTAAAG AGAGTAATTG    60
TTCGTTAAAA ATCTTGACAC CATTCCAAGC ATACCCCTTA TTGTACTTCA ATTAATTATC   120
ATTATATCAG CATAAACATT ATAATAAGTT TCTTGCGTGT TGGAACGTCA TTTTAGTTAT   180
TCTAAAGAGG AAATAGTTTC TTTTTTGCTC ATGACATCAG ACATCTGGAC TACTATACTG   240
GAGTTTACCT TTTCTTCTCC TCTTTTTCTT ATTGTTCCTC TAAAAAAAAT TATCACTTTT   300
TAAATGCATT AGTTAAACTT ATCTCAACAA CGTTTAAAAT TCATTTCTTG AATGCCCATT   360
ACAATGTAAT AGTATAACTT AATTAGTCGT CTCCATGAAC CATTAATACG TACGGAGTAA   420
TATAAAACAC CATTGGGGAG TTCAATTTGC AATAATTTCT TGCAAAAATG TAAAGTACCT   480
TTTTGTTCTT GCAAAATTTT ACAAATAAAA ATTTGCAGCT CTTTTTTTTC TCTCTCTCCA   540
AATACTAGCT CAAAACCCAC AAATATTTTT GAATTTATGG CATACTTTTA GAATGCGTTT   600
GATGCAACTA TTTTCCTTTA GGAAATATTC ACAACAATCT AAGACAATCA AAAAGTAGAA   660
AATAGTTTGT AAAAAGGGAT GTGGAGGACA TCTTAATCAA ATATTTTCAG TTTAAAACTT   720
GAAAATGAAA AAACACCCGA AAGGAAATGA TTCGTTCTTT AATATGTCCT ACACAATGTG   780
AATTTGAATT AGTTTGGTCA TACGGTATAT CATATGATTA TAAATAAAAA AAATTAGCAA   840
AAGAATATAA TTTATTAAAT ATTTTACACC ATACCAAACA CAACCGCATT ATATATAATC   900
TTAATTATCA TTATCACCAG CATCAACATT ATAATGATTC CCCTATGCGT TGGAACGTCA   960
TTATAGTTAT TCTAAACAAG AAAGAAATTT GTTCTTGACA TCAGACATCT AGTATTATAA  1020
CTCTAGTGGA GCTTACCTTT TCTTTTCCTT CTTTTTTTTC TTCTTAAAAA AATTATCACT  1080
TTTTAAATCT TGTATATTAG TTAAGCTTAT CTAAACAAAG TTTTAAATTC ATTTCTTAAA  1140
CGTCCATTAC AATGTAATAT AACTTAGTCG TCTCAATTAA ACCATTAATG TGAAATATAA  1200
ATCAAAAAAA GCCAAAGGGC GGTGGGACGG CGCCAATCAT TTGTCCTAGT CCACTCAAAT  1260
```

| | | | | | | |
|---|---|---|---|---|---|---|
|AAGGCCCATG|GTCGGCAAAA|CCAAACACAA|AATGTGTTAT|TTTTAATTTT|TTCCTCTTTT|1320|
|ATTGTTAAAG|TTGCAAAATG|TGTTATTTTT|GGTAAGACCC|TATGGATATA|TAAAGACAGG|1380|
|TTATGTGAAA|CTTGGAAAAC|CATCAAGTTT|TAAGCAAAAC|CCTCTTAAGA|ACTTAAATTG|1440|
|AGCTTCTTTT|GGGGCATTTT|TCTAGTGAGA|ACTAAAATG|GTGAGGATTG|CCTTTGGTAG|1500|
|CATTGGTGAC|TCTTTTAGTG|TTGGATCATT|GAAGGCCTAT|GTAGCTGAGT|TTATTGCTAC|1560|
|TCTTCTCTTT|GTGTTTGCTG|GGGTTGGGTC|TGCTATAGCT|TATAGTAAGT|AACACTTCTC|1620|
|TAATTAAACT|TGCATGCTAA|CATAAATACT|TAATCTGCTC|TAGCACTAAA|TAGTAAAAG|1680|
|AGCAATCAGG|TGCACTAAGG|TCCCATTAAT|TCGTTATGCA|CATGCCACGG|AGTCTAGAGA|1740|
|AAGACTAGAC|TGGCTCTATC|ATATTCAATT|TTACCTTACA|TTTACTAGA|TGCCGTTTTC|1800|
|TCAATCCATA|ACCGAAAACA|ACATAACTTT|TACAGTTACA|CCAAGACTGC|CTAATTAACC|1860|
|TTTTTTTTT|TTTTTTTGC|TTTGTGGGGT|GATTTGTAG|ATAAATTGAC|AGCAGATGCA|1920|
|GCTCTTGATC|CAG| | | | |1933|

( 2 ) INFORMATION FOR SEQ ID NO:4:

( i ) SEQUENCE CHARACTERISTICS:
        ( A ) LENGTH: 1859 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

| | | | | | | |
|---|---|---|---|---|---|---|
|CCCATATTCC|TCGATTTTCG|CCGAGATTCT|CTCCCATAGT|GCGGTTGCAA|CGGCCCTTGT|60|
|CTGCGAGCTC|GATACTGGTT|CGAGCTCGGC|ATTGGACCGA|GCCCTCGACC|TTGGTCCGAG|120|
|CTCGATTCTG|ACTTGGGGTC|TCGGTATTCG|GGGTGAGTGT|TGGTCGGTCT|ATGCATCTTC|180|
|GATAATCTCC|GTTTTGCCTC|GTAGTTCGAT|TTGGATATGA|GCTCGATAAT|GATACCGAGC|240|
|TTGTCATTGA|TCGGTCTTAG|AGCTCGAAGT|TCGACGCCTT|TACTTCGGAC|CTTGACCGAG|300|
|CTTGTTATGT|AGATATCCTT|TGATCGAAAC|ATTATCGTTT|TGACCAATCC|GTACGACTGA|360|
|CTCAAATCGA|TTTGACCGCA|CACAAGATTA|TTTTCGAAAG|ACCCTCGACG|TCTTGGAGTA|420|
|TAAAATAATT|TAGTAAAGAG|AGTAATTGTT|CGTTAAAAAT|CTTGACACCA|TTCCAAGCAT|480|
|ACCCCTTATT|GTACTTCAAT|TAATTATCAT|TATATCAGCA|TAAACATTAT|AATAAGTTTC|540|
|TTGCGTGTTG|GAACGTCATT|TTAGTTATTC|TAAAGAGGAA|ATAGTTTCTT|TTTTGCTCAT|600|
|GACATCAGAC|ATCTGGACTA|CTATACTGGA|GTTTACCTTT|TCTTCTCCTC|TTTTTCTTAT|660|
|TGTTCCTCTA|AAAAAAATTA|TCACTTTTTA|AATGCATTAG|TTAAACTTAT|CTCAACAACG|720|
|TTTAAAATTC|ATTTCTTGAA|TGCCCATTAC|AATGTAATAG|TATAACTTAA|TTAGTCGTCT|780|
|CCATGAACCA|TTAATACGTA|CGGAGTAATA|TAAAACACCA|TTGGGGAGTT|CAATTTGCAA|840|
|TAATTTCTTG|CAAAAATGTA|AAGTACCTTT|TTGTTCTTGC|AAAATTTTAC|AAATAAAAAT|900|
|TTGCAGCTCT|TTTTTTTCTC|TCTCTCCAAA|TACTAGCTCA|AAACCCACAA|ATATTTTGA|960|
|ATTTATGGCA|TACTTTTAGA|ATGCGTTTGA|TGCAACTATT|TTCCTTTAGG|AAATATTCAC|1020|
|AACAATCTAA|GACAATCAAA|AGTAGAAAA|TAGTTTGTAA|AAAGGGATGT|GGAGGACATC|1080|
|TTAATCAAAT|ATTTTCAGTT|TAAAACTTGA|AAATGAAAAA|ACACCCGAAA|GGAAATGATT|1140|
|CGTTCTTTAA|TATGTCCTAC|ACAATGTGAA|TTTGAATTAG|TTTGGTCATA|CGGTATATCA|1200|
|TATGATTATA|AATAAAAAAA|ATTAGCAAAA|GAATATAATT|TATTAAATAT|TTTACACCAT|1260|
|ACCAAACACA|ACCGCATTAT|ATATAATCTT|AATTATCATT|ATCACCAGCA|TCAACATTAT|1320|

-continued

| | | | | | |
|---|---|---|---|---|---|
| AATGATTCCC | CTATGCGTTG | GAACGTCATT | ATAGTTATTC | TAAACAAGAA | AGAAATTTGT | 1380
| TCTTGACATC | AGACATCTAG | TATTATAACT | CTAGTGGAGC | TTACCTTTTC | TTTTCCTTCT | 1440
| TTTTTTTCTT | CTTAAAAAAA | TTATCACTTT | TTAAATCTTG | TATATTAGTT | AAGCTTATCT | 1500
| AAACAAAGTT | TTAAATTCAT | TTCTTAAACG | TCCATTACAA | TGTAATATAA | CTTAGTCGTC | 1560
| TCAATTAAAC | CATTAATGTG | AAATATAAAT | CAAAAAAGC | CAAAGGGCGG | TGGGACGGCG | 1620
| CCAATCATTT | GTCCTAGTCC | ACTCAAATAA | GGCCCATGGT | CGGCAAAACC | AAACACAAAA | 1680
| TGTGTTATTT | TTAATTTTTT | CCTCTTTTAT | TGTTAAAGTT | GCAAAATGTG | TTATTTTGG | 1740
| TAAGACCCTA | TGGATATATA | AAGACAGGTT | ATGTGAAACT | TGGAAAACCA | TCAAGTTTTA | 1800
| AGCAAAACCC | TCTTAAGAAC | TTAAATTGAG | CTTCTTTTGG | GGCATTTTTC | TAGTGAGAA | 1859

(2) INFORMATION FOR SEQ ID NO:5:

(i) SEQUENCE CHARACTERISTICS:
        (A) LENGTH: 1385 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

| | | | | | |
|---|---|---|---|---|---|
| CCCATATCCC | CTTATTGTAC | TTCAATTAAT | TATCATTATA | TCAGCATAAA | CATTATAATA | 60
| AGTTTCTTGC | GTGTTGGAAC | GTCATTTTAG | TTATTCTAAA | GAGGAAATAG | TTTCTTTTTT | 120
| GCTCATGACA | TCAGACATCT | GGACTACTAT | ACTGGAGTTT | ACCTTTTCTT | CTCCTCTTTT | 180
| TCTTATTGTT | CCTCTAAAAA | AAATTATCAC | TTTTTAAATG | CATTAGTTAA | ACTTATCTCA | 240
| ACAACGTTTA | AAATTCATTT | CTTGAATGCC | CATTACAATG | TAATAGTATA | ACTTAATTAG | 300
| TCGTCTCCAT | GAACCATTAA | TACGTACGGA | GTAATATAAA | ACACCATTGG | GGAGTTCAAT | 360
| TTGCAATAAT | TTCTTGCAAA | AATGTAAAGT | ACCTTTTGT | TCTTGCAAAA | TTTTACAAAT | 420
| AAAAATTTGC | AGCTCTTTTT | TTTCTCTCTC | TCCAAATACT | AGCTCAAAAC | CCACAAATAT | 480
| TTTTGAATTT | ATGGCATACT | TTTAGAATGC | GTTTGATGCA | ACTATTTCC | TTTAGGAAAT | 540
| ATTCACAACA | ATCTAAGACA | ATCAAAAGT | AGAAATAGT | TTGTAAAAG | GGATGTGGAG | 600
| GACATCTTAA | TCAAATATTT | TCAGTTTAAA | ACTTGAAAAT | GAAAAAACAC | CCGAAAGGAA | 660
| ATGATTCGTT | CTTTAATATG | TCCTACACAA | TGTGAATTTG | AATTAGTTTG | GTCATACGGT | 720
| ATATCATATG | ATTATAAATA | AAAAAAATTA | GCAAAGAAT | ATAATTTATT | AAATATTTTA | 780
| CACCATACCA | AACACAACCG | CATTATATAT | AATCTTAATT | ATCATTATCA | CCAGCATCAA | 840
| CATTATAATG | ATTCCCCTAT | GCGTTGGAAC | GTCATTATAG | TTATTCTAAA | CAAGAAAGAA | 900
| ATTTGTTCTT | GACATCAGAC | ATCTAGTATT | ATAACTCTAG | TGGAGCTTAC | CTTTTCTTTT | 960
| CCTTCTTTTT | TTTCTTCTTA | AAAAAATTAT | CACTTTTTAA | ATCTTGTATA | TTAGTTAAGC | 1020
| TTATCTAAAC | AAAGTTTTAA | ATTCATTTCT | TAAACGTCCA | TTACAATGTA | ATATAACTTA | 1080
| GTCGTCTCAA | TTAAACCATT | AATGTGAAAT | ATAAATCAAA | AAAGCCAAA | GGGCGGTGGG | 1140
| ACGGCGCCAA | TCATTTGTCC | TAGTCCACTC | AAATAAGGCC | CATGGTCGGC | AAAACCAAAC | 1200
| ACAAAATGTG | TTATTTTTAA | TTTTTTCCTC | TTTTATTGTT | AAAGTTGCAA | AATGTGTTAT | 1260
| TTTTGGTAAG | ACCCTATGGA | TATATAAAGA | CAGGTTATGT | GAAACTTGGA | AAACCATCAA | 1320
| GTTTTAAGCA | AAACCCTCTT | AAGAACTTAA | ATTGAGCTTC | TTTGGGGCA | TTTTCTAGT | 1380
| GAGAA | | | | | | 1385

( 2 ) INFORMATION FOR SEQ ID NO:6:

( i ) SEQUENCE CHARACTERISTICS:
        ( A ) LENGTH: 1268 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
CCCATATATG ACATCAGACA TCTGGACTAC TATACTGGAG TTTACCTTTT CTTCTCCTCT        60
TTTTCTTATT GTTCCTCTAA AAAAAATTAT CACTTTTTAA ATGCATTAGT TAAACTTATC       120
TCAACAACGT TTAAAATTCA TTTCTTGAAT GCCCATTACA ATGTAATAGT ATAACTTAAT       180
TAGTCGTCTC CATGAACCAT TAATACGTAC GGAGTAATAT AAAACACCAT TGGGGAGTTC       240
AATTTGCAAT AATTTCTTGC AAAAATGTAA AGTACCTTTT TGTTCTTGCA AAATTTTACA       300
AATAAAAATT TGCAGCTCTT TTTTTCTCT CTCTCCAAAT ACTAGCTCAA AACCCACAA        360
TATTTTTGAA TTTATGGCAT ACTTTTAGAA TGCGTTTGAT GCAACTATTT TCCTTTAGGA       420
AATATTCACA ACAATCTAAG ACAATCAAAA AGTAGAAAAT AGTTTGTAAA AAGGGATGTG       480
GAGGACATCT TAATCAAATA TTTTCAGTTT AAAACTTGAA AATGAAAAAA CACCCGAAAG       540
GAAATGATTC GTTCTTTAAT ATGTCCTACA CAATGTGAAT TTGAATTAGT TTGGTCATAC       600
GGTATATCAT ATGATTATAA ATAAAAAAA TTAGCAAAAG AATATAATTT ATTAAATATT       660
TTACACCATA CCAAACACAA CCGCATTATA TATAATCTTA ATTATCATTA TCACCAGCAT       720
CAACATTATA ATGATTCCCC TATGCGTTGG AACGTCATTA TAGTTATTCT AAACAAGAAA       780
GAAATTTGTT CTTGACATCA GACATCTAGT ATTATAACTC TAGTGGAGCT TACCTTTTCT       840
TTTCCTTCTT TTTTTCTTC TTAAAAAAT TATCACTTTT TAAATCTTGT ATATTAGTTA         900
AGCTTATCTA AACAAAGTTT TAAATTCATT TCTTAAACGT CCATTACAAT GTAATATAAC       960
TTAGTCGTCT CAATTAAACC ATTAATGTGA AATATAAATC AAAAAAGCC AAAGGGCGGT       1020
GGGACGGCGC CAATCATTTG TCCTAGTCCA CTCAAATAAG GCCCATGGTC GGCAAAACCA      1080
AACACAAAAT GTGTTATTTT TAATTTTTC CTCTTTATT GTAAAGTTG CAAAATGTGT        1140
TATTTTTGGT AAGACCCTAT GGATATATAA AGACAGGTTA TGTGAAACTT GGAAAACCAT      1200
CAAGTTTTAA GCAAAACCCT CTTAAGAACT TAAATTGAGC TTCTTTTGGG GCATTTTCT      1260
AGTGAGAA                                                               1268
```

( 2 ) INFORMATION FOR SEQ ID NO:7:

( i ) SEQUENCE CHARACTERISTICS:
        ( A ) LENGTH: 1100 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
CCCATATTTA ATTAGTCGTC TCCATGAACC ATTAATACGT ACGGAGTAAT ATAAACACC        60
ATTGGGGAGT TCAATTTGCA ATAATTTCTT GCAAAAATGT AAAGTACCTT TTGTTCTTG       120
CAAAATTTTA CAAATAAAAA TTTGCAGCTC TTTTTTTTCT CTCTCTCCAA ATACTAGCTC      180
AAAACCCACA AATATTTTTG AATTTATGGC ATACTTTTAG AATGCGTTTG ATGCAACTAT      240
TTTCCTTTAG GAAATATTCA CAACAATCTA AGACAATCAA AAAGTAGAAA ATAGTTTGTA      300
```

-continued

| | | | | | |
|---|---|---|---|---|---|
| AAAAGGGATG | TGGAGGACAT | CTTAATCAAA | TATTTTCAGT | TTAAAACTTG | AAAATGAAAA | 360 |
| AACACCCGAA | AGGAAATGAT | TCGTTCTTTA | ATATGTCCTA | CACAATGTGA | ATTTGAATTA | 420 |
| GTTTGGTCAT | ACGGTATATC | ATATGATTAT | AAATAAAAAA | AATTAGCAAA | AGAATATAAT | 480 |
| TTATTAAATA | TTTTACACCA | TACCAAACAC | AACCGCATTA | TATATAATCT | TAATTATCAT | 540 |
| TATCACCAGC | ATCAACATTA | TAATGATTCC | CCTATGCGTT | GGAACGTCAT | TATAGTTATT | 600 |
| CTAAACAAGA | AAGAAATTTG | TTCTTGACAT | CAGACATCTA | GTATTATAAC | TCTAGTGGAG | 660 |
| CTTACCTTTT | CTTTTCCTTC | TTTTTTTCT | TCTTAAAAAA | ATTATCACTT | TTTAAATCTT | 720 |
| GTATATTAGT | TAAGCTTATC | TAAACAAGT | TTTAAATTCA | TTTCTTAAAC | GTCCATTACA | 780 |
| ATGTAATATA | ACTTAGTCGT | CTCAATTAAA | CCATTAATGT | GAAATATAAA | TCAAAAAAG | 840 |
| CCAAGGGCG | GTGGGACGGC | GCCAATCATT | TGTCCTAGTC | CACTCAAATA | AGGCCCATGG | 900 |
| TCGGCAAAAC | CAAACACAAA | ATGTGTTATT | TTTAATTTTT | TCCTCTTTTA | TTGTTAAAGT | 960 |
| TGCAAAATGT | GTTATTTTG | GTAAGACCCT | ATGGATATAT | AAAGACAGGT | TATGTGAAAC | 1020 |
| TTGGAAAACC | ATCAAGTTTT | AAGCAAAACC | CTCTTAAGAA | CTTAAATTGA | GCTTCTTTTG | 1080 |
| GGGCATTTTT | CTAGTGAGAA | | | | | 1100 |

( 2 ) INFORMATION FOR SEQ ID NO:8:

( i ) SEQUENCE CHARACTERISTICS:
        ( A ) LENGTH: 890 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

| | | | | | |
|---|---|---|---|---|---|
| CCCATATTAG | AATGCGTTTG | ATGCAACTAT | TTTCCTTTAG | GAAATATTCA | CAACAATCTA | 60 |
| AGACAATCAA | AAAGTAGAAA | ATAGTTTGTA | AAAAGGGATG | TGGAGGACAT | CTTAATCAAA | 120 |
| TATTTTCAGT | TTAAAACTTG | AAAATGAAAA | AACACCCGAA | AGGAAATGAT | TCGTTCTTTA | 180 |
| ATATGTCCTA | CACAATGTGA | ATTTGAATTA | GTTTGGTCAT | ACGGTATATC | ATATGATTAT | 240 |
| AAATAAAAAA | AATTAGCAAA | AGAATATAAT | TTATTAAATA | TTTTACACCA | TACCAAACAC | 300 |
| AACCGCATTA | TATATAATCT | TAATTATCAT | TATCACCAGC | ATCAACATTA | TAATGATTCC | 360 |
| CCTATGCGTT | GGAACGTCAT | TATAGTTATT | CTAAACAAGA | AAGAAATTTG | TTCTTGACAT | 420 |
| CAGACATCTA | GTATTATAAC | TCTAGTGGAG | CTTACCTTTT | CTTTTCCTTC | TTTTTTTCT | 480 |
| TCTTAAAAAA | ATTATCACTT | TTTAAATCTT | GTATATTAGT | TAAGCTTATC | TAAACAAAGT | 540 |
| TTTAAATTCA | TTTCTTAAAC | GTCCATTACA | ATGTAATATA | ACTTAGTCGT | CTCAATTAAA | 600 |
| CCATTAATGT | GAAATATAAA | TCAAAAAAAG | CCAAGGGCG | GTGGGACGGC | GCCAATCATT | 660 |
| TGTCCTAGTC | CACTCAAATA | AGGCCCATGG | TCGGCAAAAC | CAAACACAAA | ATGTGTTATT | 720 |
| TTTAATTTTT | TCCTCTTTTA | TTGTTAAAGT | TGCAAAATGT | GTTATTTTTG | GTAAGACCCT | 780 |
| ATGGATATAT | AAAGACAGGT | TATGTGAAAC | TTGGAAAACC | ATCAAGTTTT | AAGCAAAACC | 840 |
| CTCTTAAGAA | CTTAAATTGA | GCTTCTTTTG | GGGCATTTTT | CTAGTGAGAA | | 890 |

( 2 ) INFORMATION FOR SEQ ID NO:9:

( i ) SEQUENCE CHARACTERISTICS:
        ( A ) LENGTH: 713 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

| | | | | | | |
|---|---|---|---|---|---|---|
| CCCATATGTC | CTACACAATG | TGAATTTGAA | TTAGTTTGGT | CATACGGTAT | ATCATATGAT | 60 |
| TATAAATAAA | AAAAATTAGC | AAAAGAATAT | AATTTATTAA | ATATTTACA | CCATACCAAA | 120 |
| CACAACCGCA | TTATATATAA | TCTTAATTAT | CATTATCACC | AGCATCAACA | TTATAATGAT | 180 |
| TCCCTATGC | GTTGGAACGT | CATTATAGTT | ATTCTAAACA | AGAAAGAAAT | TTGTTCTTGA | 240 |
| CATCAGACAT | CTAGTATTAT | AACTCTAGTG | GAGCTTACCT | TTTCTTTCC | TTCTTTTTT | 300 |
| TCTTCTTAAA | AAAATTATCA | CTTTTAAAT | CTTGTATATT | AGTTAAGCTT | ATCTAAACAA | 360 |
| AGTTTAAAT | TCATTTCTTA | AACGTCCATT | ACAATGTAAT | ATAACTTAGT | CGTCTCAATT | 420 |
| AAACCATTAA | TGTGAAATAT | AAATCAAAAA | AAGCCAAAGG | GCGGTGGGAC | GGCGCCAATC | 480 |
| ATTTGTCCTA | GTCCACTCAA | ATAAGGCCCA | TGGTCGGCAA | AACCAAACAC | AAAATGTGTT | 540 |
| ATTTTAATT | TTTTCCTCTT | TTATTGTTAA | AGTTGCAAAA | TGTGTTATTT | TTGGTAAGAC | 600 |
| CCTATGGATA | TATAAAGACA | GGTTATGTGA | AACTTGGAAA | ACCATCAAGT | TTTAAGCAAA | 660 |
| ACCCTCTTAA | GAACTTAAAT | TGAGCTTCTT | TTGGGGCATT | TTTCTAGTGA | GAA | 713 |

( 2 ) INFORMATION FOR SEQ ID NO:10:

( i ) SEQUENCE CHARACTERISTICS:
        ( A ) LENGTH: 375 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

| | | | | | | |
|---|---|---|---|---|---|---|
| CCCATATAGC | TTATCTAAAC | AAAGTTTTAA | ATTCATTTCT | TAAACGTCCA | TTACAATGTA | 60 |
| ATATAACTTA | GTCGTCTCAA | TTAAACCATT | AATGTGAAAT | ATAAATCAAA | AAAAGCCAAA | 120 |
| GGGCGGTGGG | ACGGCGCCAA | TCATTTGTCC | TAGTCCACTC | AAATAAGGCC | CATGGTCGGC | 180 |
| AAAACCAAAC | ACAAAATGTG | TTATTTTAA | TTTTTCCTC | TTTTATTGTT | AAAGTTGCAA | 240 |
| AATGTGTTAT | TTTGGTAAG | ACCCTATGGA | TATATAAAGA | CAGGTTATGT | GAAACTTGGA | 300 |
| AAACCATCAA | GTTTAAGCA | AAACCCTCTT | AAGAACTTAA | ATTGAGCTTC | TTTTGGGGCA | 360 |
| TTTTTCTAGT | GAGAA | | | | | 375 |

PATHOGEN-RESISTANT TRANSGENIC PLANTS

This is a continuation of application(s) Ser. No. 08/236,678 filed on May 2, 1994, now abandoned, which is a continuation of application Ser. No. 07/770,002 filed on Oct. 4, 1991, now abandoned.

This invention was made with government support under grant number DMB 88-11077 from the National Science Foundation. The Government may have certain rights to this invention.

FIELD OF THE INVENTION

This invention relates to methods of controlling plant pathogens in general, and particularly relates to methods of controlling plant-parasitic nematodes.

BACKGROUND OF THE INVENTION

World-wide, plant-parasitic nematodes are among the most devastating pathogens of life sustaining crops. In 1984, nematodes accounted for more than $100 billion in economic losses. The United States' portion of this figure is almost $6 billion. While such monetary figures are staggering, much of this crop destruction occurs in tropical and subtropical regions where agricultural production is often a matter of life and death.

Genetic resistance to certain nematode species is available in some cultivars, but these are restricted in number and the availability of cultivars with both desirable agronomic features and resistance is limited. In addition, traditional methods for plant breeding require 5–10 years to produce a viable cultivar, while the need for new nematode control tools is immediate and critical.

The major means of nematode control has been the application of chemical nematicides. During 1982, in the United States alone over 100 million pounds of nematicide were applied to crops. Chemical nematicides are generally highly toxic compounds known to cause substantial environmental impact. In the past several years, issues such as ground water contamination, mammalian and avian toxicity, and residues in food have caused much tighter restrictions on the use of chemical nematicides. Unfortunately, in many situations there is no alternative available for growers who rely upon nematicides to protect their crop from root-knot and cyst nematodes.

Recently, it has become possible to genetically engineer crop plants resistant to particular pests. Perhaps the first example of this approach is that of viral coat protein genes introduced into tobacco. Tobacco plants genetically engineered to carry and express the Tobacco Mosaic Virus coat protein gene were shown to resist systemic infection by the intact virus. Another strategy is to utilize gene sequences that will kill or inhibit the pathogen directly. This approach has been used to produce transgenic plants that express the insect toxin gene from the bacterium *Bacillus thuringiensis* which, when ingested, causes insect gut paralysis. Although this strategy has resulted in crop cultivars resistant to certain pests, there are several disadvantages to the approach. Primarily, the constitutive expression of any "toxin" gene places upon the pest population very strong selective pressure for resistance. Another disadvantage of this approach is the negative energy balance the host plant suffers when there is no pest pressure. Finally, the constitutive global expression of toxin genes guarantees that non-target species, including humans, will be exposed to the protein product.

The present invention is based on our work in developing new ways of combatting plant pathogens.

SUMMARY OF THE INVENTION

The present approach to imparting pathogen resistance to plants is dramatically different from the foregoing strategies in that it directs a toxic compound to plant cells rather the than the pathogen itself. Thus, when a pathogen attempts to infect the plant the infected cells tend to die, thereby both inhibiting the ability of the pathogen to infect the plant and disrupting the pathogen's normal life cycle.

In view of the foregoing, a first aspect of the present invention is a recombinant pathogen-resistant plant comprising transformed plant cells. The transformed plant cells contain a heterologous DNA construct comprising an expression cassette, which construct comprises, in the 5' to 3' direction, a promoter, a structural gene positioned downstream from the promoter and operatively associated therewith, and a termination sequence positioned downstream from the structural gene and operatively associated therewith. The promoter is activated by a plant pathogen which attacks the plant, and the structural gene encodes a product toxic to the plant cells.

A second aspect of the present invention is a crop comprised of a plurality of plants as given above planted together in an agricultural field (i.e., any common environment in which pathogens are shared between plants of the crop, including a greenhouse).

A third aspect of the present invention is a method of combatting a plant pathogen in an agricultural field. The method comprises planting the field with a crop of recombinant pathogen-resistant plants as given above.

A fourth aspect of the present invention is a method of making a recombinant pathogen-resistant plant. The method comprises providing a plant cell capable of regeneration, then transforming the plant cell with a DNA construct comprising an expression cassette, which construct comprises, in the 5' to 3' direction, a promoter activated by a plant pathogen, a structural gene positioned downstream from said promoter and operatively associated therewith, and a termination sequence positioned downstream from the structural gene and operatively associated therewith. A recombinant pathogen-resistant plant is regenerated from the transformed plant cell.

A fifth aspect of the present invention is a DNA construct comprising an expression cassette, which construct comprises, in the 5' to 3' direction, a promoter activated by a plant pathogen, a structural gene positioned downstream from the promoter and operatively associated therewith, and a termination sequence positioned downstream from the structural gene and operatively associated therewith. The structural gene encodes a product toxic to plant cells.

The foregoing and other objects and aspects of this invention are explained in detail in the drawings herein and the specification set forth below.

BRIEF DESCRIPTION OF THE DRAWINGS

Regions hybridizing to the root specific cDNA clone RB7 are shown under the bars.

DETAILED DESCRIPTION OF THE INVENTION

Figure 1:
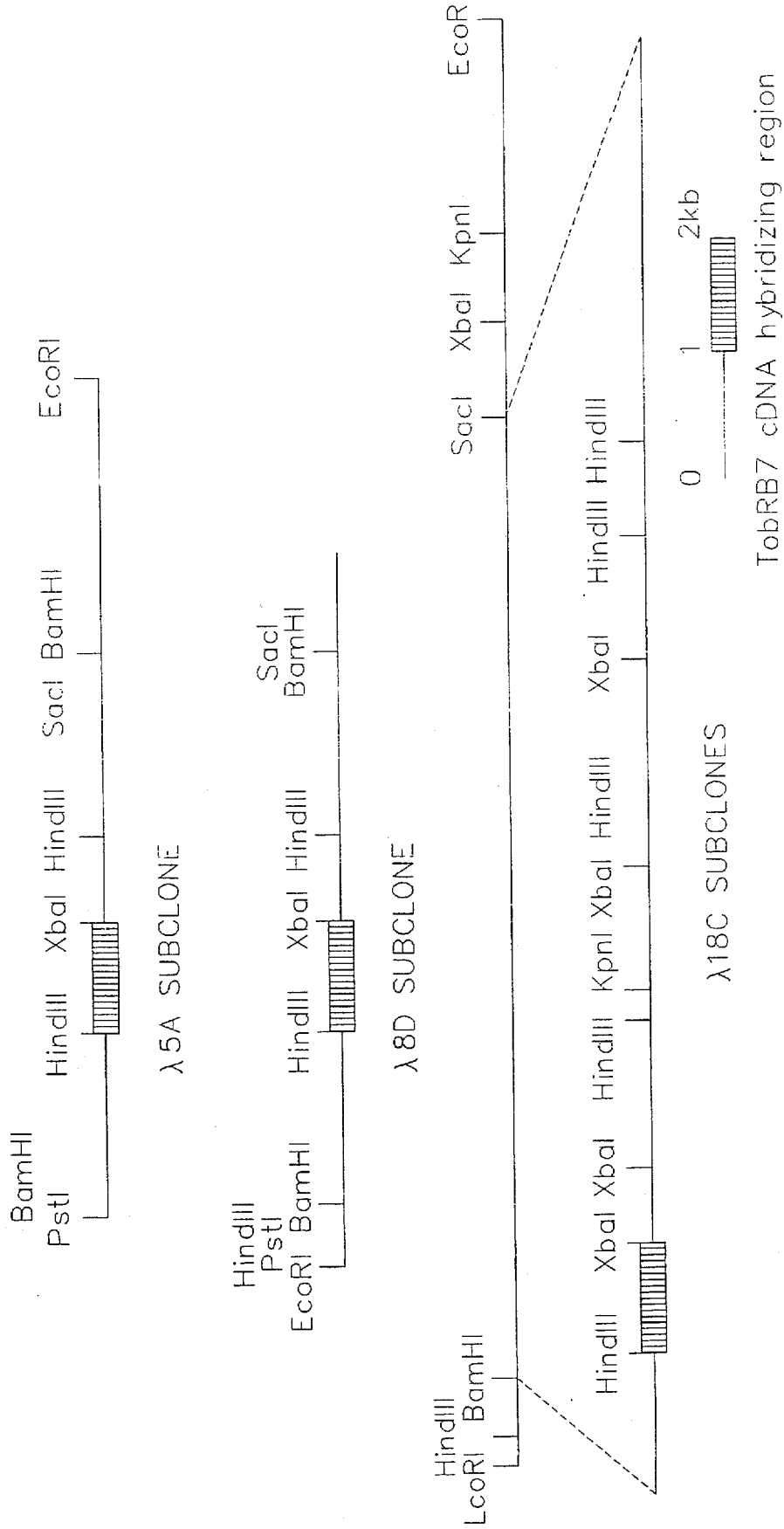
FIG. 1 shows restriction maps of genomic clones hybridizing to the root-specific cDNA clone TobRB7. Genomic clones were restriction mapped for BamHI (B), HindIII (H), PstI (P), EcoRI (R), and SalI (S).

Plant pathogens which may be combatted by the method of the present invention include bacteria, viruses, fungi, and nematodes. The pathogens may be those which attack any tissue of the plant, including leaf and root, but the invention is contemplated to be particularly useful for combatting pathogens which attack (or infect) the root. The present invention may be carried out with a variety of plants, both monocols and dicots, preferably dicots.

The invention may be illustrated with respect to nematodes, particularly the root knot nematodes (Meloidogyne spp.) and the cyst nematodes (Globodera spp. and Heterodera spp.), which have similar life cycles. Root-knot nematodes are sedentary endoparasites with an extremely intimate and complex relationship to the host plant. The infective second stage juvenile (J2) is free in the soil. Upon location of a host root, the J2 penetrates the root intercellularly in the region just posterior to the root cap and migrates to the developing vascular cylinder. The nematode then orients itself parallel to the cylinder and injects glandular secretions into the plant cells surrounding its head, resulting in the initiation of nematode feeding cells. These 5–7 cells undergo rapid nuclear divisions, increase tremendously in size, and become filled with pores and cell wall invaginations. The feeding site cells, or "giant cells", function as super transfer cells to provide nourishment to the developing nematode. During this time, the nematode loses the ability to move and swells from the normal eel shaped J2 to a large, pear shaped adult female. As the nematode feeds on the giant cells, parthenogenic reproduction results in the disposition of 300–400 eggs. This entire process occurs over the span of 20–30 days, and root-knot nematodes may complete as many as 7 generations during a cropping season. The life cycle of the cyst nematode is essentially the same, except that its feeding site is referred to as a "syncytia", and it undergoes sexual reproduction. It will be seen that, by causing the plant itself to kill or disable the cells upon which the pathogen must feed, the pathogen will be much less successful at infecting the plant.

The pathogen-inducible promoters (or "pathogen-responsive elements") of two gene types may be employed in the present invention: (a) genes not normally expressed in plant tissues, but expressed in response to pathogen infection; and (b) genes normally expressed in plant tissues whose expression is increased in response to pathogen infection. A variety of screening strategies allow the isolation of genes, and their corresponding pathogen-responsive elements of either type. See, e.g., M. Conkling et al., *Plant Physiol.* 93, 1203–1211 (1990); S. Gurr et al., *Mol. Gen. Genet.* 226, 361–366 (1991). Screening may be carried out with the polymerase chain reaction procedure, as described in U.S. Pat. Nos. 4,683,185 and 4,683,202, the disclosures of which are to be incorporated herein by reference, or by low stringency hybridization procedures (e.g., hybridization procedures in which probes are capable of hybridizing to sequences to which they are 60% homologous, such as procedures characterized by a wash stringency of 5×SSC, 25% Formamide and 0.1% SDS at 42° C.). In general, a cDNA library from the mRNA of a pathogen-infected plant tissue is differentially screened with probes generated from CDNA obtained from the mRNA of (a) plant tissue (e.g., plant root tissue) infected with the pathogen and (b) corresponding plant tissue not infected with that pathogen to identify clones of genes which exhibit greater expression in pathogen-infected plants. The pathogen-responsive elements of these genes are then identified by deletion analysis. These elements may in turn be used to screen cDNA libraries of other plants and other plant tissues at low stringency for homologous pathogen-responsive elements.

Hybridization procedures are available which allow for the isolation of cDNA clones whose mRNA levels are as low as about 0.05% of poly(A+)RNA. See M. Conkling et al., supra. In brief, CDNA libraries are screened using single-stranded cDNA probes of reverse transcribed mRNA from plant tissue (i.e., roots and leaves). For differential screening, a nitrocellulose or nylon membrane is soaked in 5×SSC, placed in a 96 well suction manifold, 150 μL of stationary overnight culture transferred from a master plate to each well, and vacuum applied until all liquid has passed through the filter. 150 μL of denaturing solution (0.5M NaOH, 1.5M NaCl) is placed in each well using a multiple pipetter and allowed to sit about 3 minutes. Suction is applied as above and the filter removed and neutralized in 0.5M Tris-HCl (pH 8.0), 1.5M NaCl. It is then baked 2 hours in vacuo and incubated with the relevant probes. By using nylon membrane filters and keeping master plates stored at −70° C. in 7% DMSO, filters may be screened multiple times with multiple probes and appropriate clones recovered after several years of storage.

For example, to isolate genes whose expression is induced or enhanced by nematode infection, a cDNA library of mRNA isolated from nematode infected tobacco roots is constructed. The roots are staged such that mRNA is isolated at the time of giant cell initiation.

The library is then screened by the procedures given above using single stranded CDNA probes of MRNA isolated from nematode-infected and control roots. Those CDNA clones exhibiting differential expression are then used as probes on tobacco genomic Southern blots (to confirm the CDNA corresponds to tobacco and not nematode transcripts) and Northern blots of root RNA from infected and control tissue (to confirm differential expression). Those clones exhibiting differential expression are then used as probes to screen an existing tobacco genomic library. Essentially the same procedure is carried out with plants other than tobacco and nematodes (or other pathogens) other than root-knot nematodes. The procedure is useful for identifying promoters induced by cyst nematodes, in which case the roots are staged such that mRNA is isolated at the time of syncytia initiation. For example, a potato-cyst nematode (Globodera spp.) inducible promoter is isolated from potato plants (*Solanum tuberosum*) in accordance with the foregoing procedures. See, e.g., S. Gurr et al., supra.

While a particularly preferred promoter for carrying out the present invention is the nematode-responsive element of the TobRB7 promoter, also useful in the present invention are promoters and pathogen-responsive elements isolated from other tobacco genes, or from plants other than tobacco as set forth below, which are homologous to the TobB7 promoter nematode responsive element and are capable of directing transcription of a downstream structural gene in a plant cell in response to nematode infection. RB7 promoter sequences and their nematode-responsive elements may be obtained from other plant species by using TobRB7 structural gene segments as probes to screen for homologous structural genes in other plants by DNA hybridization under low stringency conditions, as given above. Alternatively, regions of the TobRB7 structural gene which are conserved among species are used as PCR primers to amplify a longer segment from a species other than Tobacco, and that longer segment used as a hybridization probe (the latter approach permitting higher stringency screening). Examples of plant species which may be used in accordance with the foregoing procedures to generate additional RB7 sequences include soybean, potato, cotton, sugarbeet, sunflower, carrot, celery, flax, cabbage and other cruciferous plants, pepper, tomato, citrus trees, bean, strawberry, lettuce, maize, alfalfa, oat, wheat, rice, barley, sorghum and canola. RB7 nematode-responsive elements from other plants are generally those which are at least about 75 percent homologous, more particularly at least about 85 percent homologous, and most particularly at least about 90 percent homologous, to a 50 base segment of the Tobacco RB7 promoter capable of directing nematode-responsive expression of a downstream structural gene in a plant cell. By "50 base segment" is meant a continuous portion of the TobRB7 promoter, or the nematode-responsive element thereof, which is 50 nucleotides in length.

Another illustrative promoter, where the pathogen is a geminivirus, is the AL2 promoter of the geminiviruses, which is activated by the geminivirus AL3 protein. Hence, the geminivirus AL2 promoter serves as a geminivirus responsive element responding to AL3.

An advantage of the present invention is that two or more promoters can be "daisychained" to a single structural gene. Where each promoter is responsive to a different pathogen, the plant is then provided with resistance to a plurality of promoters. For example, a second promoter may be positioned upstream from the structural gene and operatively associated therewith so that the structural gene is associated with a plurality of promoters, with each of the promoters activated by a different plant pathogen. Still more promoters can be included if desired.

The term "operatively associated," as used herein, refers to DNA sequences on a single DNA molecule which are associated so that the function of one is affected by the other. Thus, a promoter is operatively associated with a structural gene when it is capable of affecting the expression of that structural gene (i.e., the structural gene is under the transcriptional control of the promoter). The promoter is said to be "upstream" from the structural gene, which is in turn said to be "downstream" from the promoter.

DNA constructs, or "expression cassettes," of the present invention include, 5'-3' in the direction of transcription, a promoter as discussed above, a structural gene operatively associated with the promoter, and, optionally, a termination sequence including stop signal for RNA polymerase and a polyadenylation signal for polyadenylase (e.g., the nos terminator). All of these regulatory regions should be capable of operating in the cells of the tissue to be transformed. The 3' termination region may be derived from the same gene as the transcriptional initiation region or may be derived from a different gene.

Structural genes are those portions of genes which comprise a DNA segment coding for a protein, polypeptide, or portion thereof, possibly including a ribosome binding site and/or a translational start codon, but lacking a promoter. The term can also refer to copies of a structural gene naturally found within a cell but artificially introduced. The structural gene may encode a protein not normally found in the plant cell in which the gene is introduced or in combination with the promoter to which it is operationally associated, in which case it is termed a heterologous structural gene. Genes which may be operationally associated with a promoter of the present invention for expression in a plant species may be derived from a chromosomal gene, cDNA, a synthetic gene, or combinations thereof.

Structural genes employed in carrying out the present invention encode a product which is toxic to plant cells. A wide variety of protein or peptide products which are toxic to plant cells can be used, including (but not limited to) enzymes capable of degrading nucleic acids (DNA, RNA) such as nucleases, restriction endonucleases micrococcal nucleas, Rnase A, and barnase; enzymes which attack proteins such as trypsin, pronase A, carboxypeptidase, endoproteinase Asp-N, endoproteinase Glu-C, and endoproteinase Lys-C; ribonucleases such as RNase CL-3 and RNase $T_1$, toxins from plant pathogenic bacteria such as phaseolotoxin, tabtoxin, and syringotoxin; lipases such as produced from porcine pancrease and *Candida cyclindracea*, membrane channel proteins such as glp F and connexins (gap junction proteins, and antibodies which bind proteins in the cell so that the cell is thereby killed or debilitated. Genes which produce antibodies to plant cell proteins can be produced as described in W. Huse et al., *Science* 246, 1275–1281 (1989). Proteins to which such antibodies can be directed include, but are not limited to, RNA polymerase, respiratory enzymes, cytochrome oxidase, Krebs cycle enzymes, protein kinases, aminocyclopropane-1-carboxylic acid synthase, and enzymes involved in the shikimic acid pathway such as enolpyruvyl shikimic acid-5-phosphate synthase.

Particularly preferred is a structural gene encoding mature Bacillus amyloliquefaciens RNase (or Barnase). See, e.g., C. Mariani et al., *Nature* 347, 737–741 (1990); C. Paddon and R. Hartley, *Gene* 40, 231–39 (1985). The toxic product may either kill the plant cell in which it is expressed or simply disable the cell so that it is less capable of supporting the pathogen. It is preferred, particularly where the plant is a food plant, that the plant-toxic product be non-toxic to animals, and particularly be non-toxic to humans.

Where the expression product of the structural gene is to be located in a cellular compartment other than the cytoplasm, the structural gene may be constructed to include regions which code for particular amino acid sequences which result in translocation of the product to a particular site, such as the cell plasma membrane, or may be secreted into the periplasmic space or into the external environment of the cell. Various secretory leaders, membrane integration sequences, and translocation sequences for directing the peptide expression product to a particular site are described in the literature. See, for example, Cashmore et al., *Bio/Technology* 3, 803–808 (1985), Wickner and Lodish, *Science* 230, 400–407 (1985).

The expression cassette may be provided in a DNA construct which also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant host. The markers may be protection against a biocide, such as antibiotics, toxins, heavy metals, or the like; provide complementation, by imparting prototrophy to an auxotrophic host: or provide a visible phenotype through the production of a novel compound in the plant. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are beta-glucuronidase, providing indigo production, luciferase, providing visible light production, NPTII, providing kanamycin resistance or G418 resistance, HPT, providing hygromycin resistance, and the mutated aroA gene, providing glyphosate resistance.

The various fragments comprising the various constructs, expression cassettes, markers, and the like may be introduced consecutively by restriction enzyme cleavage of an appropriate replication system, and insertion of the particular construct or fragment into the available construct r ligation and cloning the DNA construct may be isolated for further manipulation. All of these techniques are amply exemplified in the literature and find particular exemplification in Maniatis et al., Molecular Cloning: A Laboratory Manual, Cold Spring Harbor Laboratory, Cold Spring Harbor, N.Y., 1982.

Vectors which may be used to transform plant tissue with DNA constructs of the present invention include both Agrobacterium vectors and ballistic vectors, as well as vectors suitable for DNA-mediated transformation.

*Agrobacterium tumefaciens* cells containing a DNA construct of the present invention, wherein the DNA construct comprises a Ti plasmid, are useful in methods of making transformed plants. Plant cells are infected with an *Agrobacterium tumefaciens* as described above to produce a transformed plant cell, and then a plant is regenerated from the transformed plant cell. Numerous Agrobacterium vector systems useful in carrying out the present invention are known. For example, U.S. Pat. No. 4,459,355 discloses a method for transforming susceptible plants, including dicots, with an Agrobacterium strain containing the Ti plasmid. The transformation of woody plants with an Agrobacterium vector is disclosed in U.S. Pat. No. 4,795,855. Further, U.S. Pat. No. 4,940,838 to Schilperoort et al. discloses a binary Agrobacterium vector (i.e., one in which the Agrobacterium contains one plasmid having the vir region of a Ti plasmid but no T region, and a second plasmid having a T region but no vir region) useful in carrying out the present invention.

Microparticles carrying a DNA construct of the present invention, which microparticle is suitable for the ballistic transformation of a plant cell, are also useful for making transformed plants of the present invention. The microparticle is propelled into a plant cell to produce a transformed plant cell, and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Agracetus European Patent Application Publication No. 0,270,356, titled *Pollen-mediated Plant Transformation*. When using ballistic transformation procedures, the expression cassette may be incorporated into a plasmid capable of replicating in the cell to be transformed. Examples of microparticles suitable for use in such systems include 1 to 5 μm gold spheres. The DNA construct may be deposited on the microparticle by any suitable technique, such as by precipitation.

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

Plants which may be employed in practicing the present invention include (but are not limited to) tobacco (*Nicotiana tabacum*), potato (*Solanum tuberosum*), soybean (*glycine max*), peanuts (*Arachis hypogaea*), cotton (*Gossypium hirsutum*), sweet potato (*Ipomoea batatus*), cassava (*Manihot esculenta*), coffee (*Cofea spp.*), coconut (*Cocos nucifera*), pineapple (*Ananas comosus*), citrus trees (Citrus spp.), cocoa (*Theobroma cacao*), tea (*Camellia sinensis*), banana (Musa spp.), Avocado (*Persea americana*), Fig (*Ficus casica*), Guava (*Psidium guajava*), Mango (*Mangifera indica*), Olive (*Olea europaea*), papaya (*Carica papaya*), Cashew (*Anacardium occidentale*), Macadamia (*Macadamia integrifolia*), Almond (*Prunus amygdalus*), sugar beets (*Beta vulgaris*), corn (*Zea mays*), wheat, oats, rye, barley, rice, vegetables, ornamentals, and conifers. Vegetables include tomatoes (*Lycopersicon esculentum*), lettuce (e.g., *Lactuea sativa*), green beans (*Phaseolus vulgaris*), lima beans (*Phaseolus limensis*), peas (Lathyrus spp.) and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petnunias (*Petunia hybrida*), carnation (*dianthus caryophyllus*), poinsettia (*Euphorbia pulcherima*), and chyrsanthemum. Conifers which may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea*

*glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Some plants-parasitic nematodes from which plants may be protected by the present invention, and the corresponding plants, are as follows: Alfalfa: *Ditylenchus dipsaci, Meloidogyne hapla, Meloidogyne incognita, Meloidogyne javanica,* Pratylenchus spp., Paratylenchus spp., and Xiphinema spp.; Banana: *Radopholus similis, Helicotylenchus multicinctus, Meloidogyne incognita, M. arenaria, M. javanica, Pratylenchus coffeae,* and *Rotylenchulus reniformis*; Beans & peas: Meloidogyne spp., Heterodera spp., Belonolaimus spp., Helicotylenchus spp., *Rotylenchulus reniformis, Paratrichodorus anemones,* and Trichodorus spp.; cassava: *Rotylenchulus reniformis,* Meloidogyne spp. cereals: *Anguina tritici* (Emmer, rye, spelt wheat), *Bidera avenae* (oat, wheat), *Ditylenchus dipsaci* (rye, oat), *Subanguina radicicola* (oat, barley, wheat, rye), *Meloidogyne naasi* (barley, wheat, rye), Pratylenchus spp. (oat, wheat, barley, rye), Paratylenchus spp. (wheat), Tylenchorhynchus spp. (wheat, oat); chickpea: *Heterodera cajani, Rotylenchulus reniformis, Hoplolaimus seinhorsti,* Meloidogyne spp., Pratylenchus spp.; Citrus: *Tylenchulus semipenetrans, Radopholus similis, Radopholus citrophilus* (Florida only), *Hemicycliophora arenaria.* Pratylenchus spp., Meloidogyne spp., *Bolonolaimus longicaudatus* (Florida only), Trichodorus, Paratrichodorus, Xiphinema spp.; clover: Meloidogyne spp., *Heterodera trifolii*; coconut: *Rhadinaphelenchus cocophilus*; coffee: *Meloidogyne incognita* (Most important in Brazil), *M. exigua* (widespread), *Pratylenchus coffeae, Pratylenchus brachyurus, Radopholus similis, Rotylenchulus reniformis,* Helicotylenchus spp.; corn: Pratylenchus spp., *Paratrichodorus minor,* Longidorus spp., *Hoplolaimus columbus*; cotton: *Meloidogyne incognita, Belonolaimus longicaudatus, Rotylenchulus reniformis, Hoplolaimus galeatus,* Pratylenchus spp., Tylenchorhynchus spp.,*Paratrichodorus minor*; grapes: Xiphinema spp., *Pratylenchus vulnus,* Meloidogyne spp., *Tylenchulus semipenetrans, Rotylenchulus reniformis*; grasses: Pratylenchus spp., Longidorus spp., *Paratrichodorus christiei,* Xiphinema spp., Ditylenchus spp.; peanut: Pratylenchus spp., *Meloidogyne hapla., Meloidogyne arenaria,* Criconemella spp., *Belonolaimus longicaudatus* (in Eastern United States); pigeonpea: *Heterodera cajani, Rotylenchulus reniformis, Hoplolaimus seinhorsti,* Meloidogyne spp., Pratylenchus spp.; pineapple: *Paratrichodorus christiei,* Criconemella spp., Meloidogyne spp., *Rotylenchulus reniformis,* Helicotylenchus spp., Pratylenchus spp., Paratylenchus spp.; potato: *Globodera rostochiensis, Globodera pallida,* Meloidogyne spp., Pratylenchus spp., *Trichodorus primitivus,* Ditylenchus spp., Paratrichodorus spp., *Nacoabbus aberrans*; rice: *Aphelenchiodes besseyi, Ditylenchus angustus,* Hirchmanniella spp., *Heterodera oryzae,* Meloidogyne spp. small fruits: Meloidogyne spp.; Pratylenchus spp., Xiphinema spp., Longidorus spp., *Paratrichodorus christiei,* Aphelenchoides spp. (strawberry); soybean: *Heterodera glycines, Meloidogyne incognita, Meloidogyne javanica,* Belonolaimus spp., *Hoplolaimus columbus*; sugar beet: *Heterodera schachtii, Ditylenchus dipsaci,* Meloidogyne spp., *Nacobbus aberrans,* Trichodorus spp., Longidorus spp., Paratrichodorus spp.; sugar cane: Meloidogyne spp., Pratylenchus spp., Radopholus spp., Heterodera spp., Hoplolaimus spp., Helicotylenchus spp., Scutellonema spp., Belonolaimus spp., Tylenchorhynchus spp., Xiphinema spp., Longidorus spp., Paratrichodorus spp.; tea: Meloidogyne spp., Pratylenchus spp., *Radopholus similis, Hemicriconemoides kanayaensis,* Helicotylenchus spp., *Paratylenchus curvitatus*; tobacco: Meloidogyne spp., Pratylenchus spp., *Tylenchorhynchus claytoni, Globodera tabacum,* Trichodorus spp., *Xiphinema americanum, Ditylenchus dipsaci* (Europe only), Paratrichodorus spp.; tomato: Pratylenchus spp., Meloidogyne spp.; tree fruits: Pratylenchus spp. (apple, pear, stone fruits), Paratylenchus spp. (apple, pear), Xiphinema spp. (pear, cherry, peach), *Cacopaurus pestis* (walnut), Meloidogyne spp. (stone fruits, apple, etc.), Longidorus spp. (cherry), Criconemella spp. (peach), and Tylenchulus spp. (olive).

In addition to nematodes, the present invention can be employed to combat plant pathogenic viruses, plant pathogenic bacteria, and plant pathogenic fungi. See generally G. Agrios, *Plant Pathology* (3d Ed., Academic Press, Inc.). Examples of plant viruses which may be combatted by the present invention include single stranded RNA viruses (with and without envelope), double stranded RNA viruses, and single and double stranded DNA viruses such as (but not limited to) tobacco mosaic virus, tobacco rattle virus, pea enation mosaic virus, barley stripe mosaic virus, potato viruses X and Y, carnation latent virus, beet yellows virus, maize chlorotic virus, tobacco necrosis virus, turnip yellow mosaic virus, tomato bushy stunt virus, southern bean mosaic virus, barley yellow dwarf virus, tomato spotted wilt virus, lettuce necrotic yellows virus, wound tumor virus, maize streak virus, and cauliflower mosaic virus. Examples of plant pathogenic bacteria which can be combatted by the present invention include (but are not limited to) Agrobacterium spp., Clavibacter (or Corynebacterium) spp., Erwinia spp., Peudomonas spp., Xanthomonas spp., Streptomyces spp., and Xylella spp. Examples of plant pathogenic fungi which can be combatted by the present invention, and some of the plants which can be protected therefrom by the present invention, include (but are not limited to) Fuligo spp., Mucilago spp., Physarum spp., *Plasmodiophora brassicaea* (causes clubroot of crucifers), *Polymyxa graminis* (parasitic in wheat and other cereals), *Spongospora subterranea* (causes powdery scab of potato tubers), *Olpidium brassicae* (parasitic in roots of cabbage), *Physoderma maydis* (causes brown spot of corn), *Sychytrium endobioticum, Urophylytis alfalfae,* Aphanomyces spp. (causes root rot in many vegetables), *Phytophthora infestans, Albugo candida, Peronospora nicotianae, Bermia lactucae, Sclerospora graminicola, Pseudoperonospora cubensis,* Rhizopus spp. (causes soft rot of fruits and vegetables), *Choanephora cucurbitarum, Saccharomyces cerevisiae, Podosphaera leucotricha* (causes powdery mildew of apple), *Spaerotheca pannosa* (causes powdery mildew of roses and peach), *Hypoxylon mammatum* (causes canker of poplars), *Cochliobolus sativus* (causes leaf spots and root rots on grain crops), *Diplocarpon rosae* (causes black spot of roses), Lophodermium spp. (causes pine needle blight), *Diplodia maydis* (causes stalk and ear rot of corn), *Botrytis cinerea* (causes gray mold), *Graphium ulmi* (causes Dutch elm disease; sexual stage is Ceratocystis), Ustilago spp. (causes smut of corn, wheat, barley, etc.), and *Armillaria mellea* (causes root rots of forest and fruit trees).

Those skilled in the art will appreciate that the RB7 nematode-responsive elements disclosed herein may be employed in other strategies, such as in activating genes which produce an insect toxin such as a *Bacillus thuringiensis* toxin. Thus, the present invention provides recombinant pathogen-resistant plants comprising transformed plant cells, wherein the transformed plant cells contain a heterologous DNA construct comprising an expression cassette, which construct comprises, in the 5' to 3' direction, a promoter, a structural gene positioned downstream from the promoter and operatively associated therewith, and a termination sequence positioned downstream from the structural gene and operatively associated therewith. The promoter comprises the RB7 nematode-responsive element, and the structural gene encodes a product toxic to the nematode such as a *Bacillus thuringiensis* toxin. Such plants can be made and used essentially as described above.

The examples which follow are set forth to illustrate the present invention, and are not to be construed as limiting thereof.

EXAMPLE 1

Isolation and Expression of Genomic Root-Specific Clone RB7

*Nicotiana tabacum* cv Wisconsin 38 was used as the source of material for cloning and gene characterization. Genomic DNA was partially digested with Sau3A and size-fractionated on 5 to 20% potassium acetate gradients. Size fractions of 17 to 23 kb were pooled and ligated into the λ vector, EMBL3b that had been digested with BamHI and EcoRI. See A. Frischauf et al., J. Mol. Biol. 170, 827–842 (1983). A primary library of approximately $3.5 \times 10^6$ recombinants was screened by plaque hybridization. Positive clones were plaque purified. Restriction maps of the genomic clones were constructed using the rapid mapping procedure of Rachwitz et al., Gene 30, 195–200 (1984).

Regions encoding the root-specific clones were identified by Southern blots. To further define the transcribed regions, we took advantage of the fact that the genes are expressed at high levels. Thus, probes made of cDNA of reverse transcribed poly(A+)RNA would hybridize to Southern blots of restricted genomic clones in a manner analogous to differential screening experiments. See F. Kilcherr, Nature 321, 493–499 (1986). The clones were digested with the appropriate restriction enzymes and the fragments separated on agarose gels. These fragments were then Southern blotted to nitrocellulose filters and probed with reverse transcribed root poly(A+)RNA. The probe was primed using random hexanucleotides (Pharmacia Biochemicals, Inc.) such that the 3' termini of the mRNA molecules would not be over represented among the probe.

Clones hybridizing to each root-specific cDNA clone were plaque purified. Preliminary restriction maps of some of the isolated genomic clones are shown in FIG. 1. Comparisons of the restriction maps of the genomic clones (FIG. 1) with genomic Southern hybridization experiments (not shown) reveal a good correlation of the sequences hybridizing to the root-specific CDNA clones. Clones λ5A and λ18D appear overlapping and, along with λ18C, hybridize to the CDNA clone TobRB7. All of the fragments hybridizing strongly to TobRB7 in genomic Southern hybridization experiments may be accounted for by those hybridizing from the genomic clones, suggesting that the genomic sequences encoding this cDNA have been isolated. Note that clone λ18C, though encoding a different gene from clones λ5A and λ8D, shows about 90% nucleotide sequence homology in the first 800 base pairs upstream from the structural gene.

Clone 15A was designated as TobRB7-5A (SEQ ID NO:1) and used to generate the promoter sequences employed in the experiments described below. This clone is hypothesized to code for a cell membrane channel protein (SEQ ID NO:2).

EXAMPLE 2

Root-Specific Expression of an Exogenous Reporter Gene with the TobRB7 Promoter

The ability of the TobRB7 promoter region of the λ15A genomic clone to regulate the expression of a heterologous reporter gene was tested by cloning approximately 1.4 kb of 5' flanking sequence into pBI101.2 In brief, a TobRB7 5' flanking region (SEQ ID NO:3) was isolated from λ5A and fused with β-glucuronidase in the Agrobacterium binary vector, pBI 101.2. This vector contains a β-glucuronidase (GUS) reporter gene and an nptII selectable marker flanked by the T-DNA border sequences (R. Jefferson et al., EMBO J. 6, 3901–3907 (1987)). The construction was mobilized into an Agrobacterium host that carries a disarmed Ti-plasmid (LBA4404) capable of providing (in trans) the vir functions required for T-DNA transfer and integration into the plant genome, essentially as described by An et al., in S. Belvin and R. Schilperoot, eds., Plant Molecular Biology Manual, Martinus Nijhoff, Dordrecht, The Netherlands, pp A3-1-19 (1988). *Nicotiana tabacum* SR1 leaf discs were infected and transformants selected and regenerated as described by An et al., Plant Physiol. 81, 301–305 (1986). Whole plants or excised root and leaf tissue were assayed for GUS expression according to Jefferson et al., supra. For histochemical staining, plants were incubated in the 5-bromo-4-chloro-3-indolyl β-D-glucuronide (X-GLUC) at 37° C. overnight. Tissues expressing GUS activity cleave this substrate and thereby stain blue. After the incubation the tissues were bleached in 70% ethanol. GUS enzyme activities were measured using the fluorogenic assay described by Jefferson et al.

Table 1 below presents GUS activity measurements of roots and leaves from five independent transformants. Although variable expression levels are observed from transformant to transformant, in all cases GUS activity is root-specific, demonstrating that these sequences are sufficient for regulated gene expression.

TABLE 1

Organ-Specific Expression of GUS Activity in Transgenic Plants

| Transgenic Plant No. | GUS Activity | |
|---|---|---|
| | Roots pmol MU/mg | Leaves protein/min |
| 1 | 100 | ND[a] |
| 2 | 170 | ND |
| 3 | 200 | ND |
| 4 | 100 | ND |
| 5 | 530 | ND |
| Nontransformed | ND | ND |

[a]Not detectable.

EXAMPLE 3

Deletion Analysis of the TobRB7 Promoter

These experiments were carried out in essentially the same manner as the experiments described in Example 2 above, except that (a) the length of the TobRB7 flanking region employed was varied to explore how various portions of the flanking region affected expression of GUS, and (b) the TobRB7 structural gene was completely removed and the TobRB7 flanking regions fused to the GUS initiating methionene codon.

Figure 2:
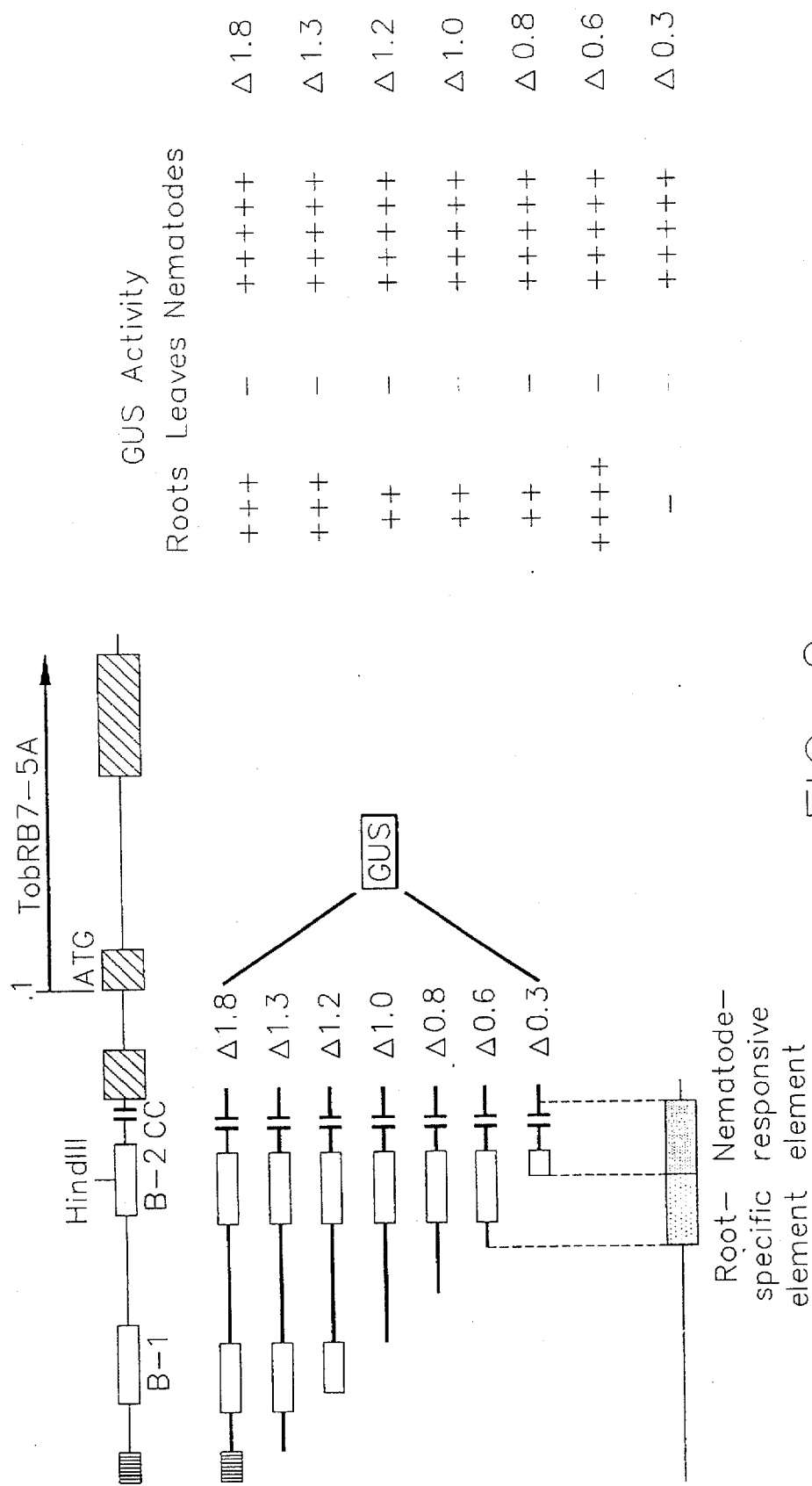
FIG. 2 schematically illustrates the deletion analysis of the genomic RB7 promoter sequence. RB7 flanking regions of various lengths where prepared and coupled to a β-Glucuronidase (GUS) gene, transgenic plants prepared with the construct, and GUS activity assayed in both the roots and the leaves of the transgenic plants. Results are summarized on the right-hand side of the FIG.

Deletion mutants employed as promoter sequences in these experiments are graphically summarized in FIG. 2. These deletion mutants are designated as Δ1.8 (SEQ ID NO:4), Δ1.3 (SEQ ID NO:5), Δ1.2 (SEQ ID NO: 6), Δ1.0 (SEQ ID NO:7), Δ0.8 (SEQ ID NO:8), Δ0.6 (SEQ ID NO:9), and Δ0.3 (SEQ ID NO:10).

The activity of these various mutants is summarized in the right-hand portion of FIG. 2. Note that the greatest root-specific expression was obtained with the Δ0.6 deletion mutant, indicating the presence of an upstream silencer region. GUS activity data is presented in detail in Table 2 below. Note that only Δ0.3 (SEQ ID NO:10) was inactive as a promoter, indicating that the TobRB7 promoter is found in the region extending about 800 nucleotides upstream from the TobRB7 structural gene. However, the Δ0.3 deletion mutant contains the RB7 nematode-responsive element, as discussed below.

TABLE 2

AVERAGE GUS ACTIVITY
(Range of activities)

| | No. of Plants | ROOTS | LEAVES | Median Ratio (Roots/Leaves) |
|---|---|---|---|---|
| Wild Type | 8 | 4 (1–11) | 0.7 (0.17–2.26) | 2.8 |
| pBI-0.0 | 21 | 187 (4–614) | 6.9 (0.18–95.7) | 19.0 |
| pBI-0.3 | 21 | 160 (1–586) | 5.2 (0.8–28.4) | 21.1 |
| pBI-0.6 | 22 | 2242 (4–11,540) | 24.7 (0.05–217.5) | 122.3 |
| pBI-0.8 | 17 | 652 (2–3394) | 4.8 (0.03–23.5) | 103.2 |
| pBI-1.0 | 9 | 804 (3–2068) | 55.7 (1.72–373.4) | 97.1 |
| pBI-1.2 | 23 | 881 (2–4688) | 4.3 (0.14–22.4) | 113.5 |
| pBI-1.3 | 24 | 1475 (5–14,110) | 3.0 (0.14–8.9) | 166.4 |
| pBI-1.8 | 18 | 1007 (1–4274) | 6.5 (0.3–20.0) | 121.3 |

EXAMPLE 4

Localization of Gene Activation in Nematode Infected Plants

Transgenic tobacco plants prepared as described in Examples 2 and 3 above were infected with tobacco root-knot nematodes (*Meloidogyne incognita*) in accordance with known techniques. See, e.g., C. Opperman et al., *Plant Disease*, 869–871 (October 1988). Roots were stained for GUS activity (blue) and nematodes were stained red at three stages: (a) 24–48 hours post infection; (b) 7–10 days post infection; and (c) 20–25 days post infection. Nematodes were stained after GUS staining by incubating roots in 95% ethanol/glacial acetic acid (1:1) plus five drops of acid fushsin (per 100 mLs) for four hours, then destained in a saturated chloral hydrate solution for twelve hours to overnight.

GUS activity was generally found in the elongation zone of the root. At 24–48 hours post infection, second stage juvenile nematodes have penetrated the tobacco roots, are in the corticle tissue and are migrating in search of an appropriate feeding site. Juveniles in the vascular tissue at this stage have already begun to establish feeding sites. At 7–10 days post infection, swollen late second stage juveniles are seen with their heads in the feeding site. At 20–25 days post infection, adult nematodes are seen protruding from galled root tissue, with their head still embedded in the vascular tissue and the posterior exposed to allow egg deposition.

GUS activity in nematode infected root tissue of plants transformed with the various deletion mutants described in Example 3 indicated that the nematode-responsive element of the TobRB7 promoter is located in the Δ0.3 (SEQ ID NO:10) deletion mutant.

Similar results are obtained with the peanut root-knot nematode (*Meloidogyne arenaria*).

During the foregoing experiments, it was observed that duration of gene expression in nematode-infected plants was much longer than in uninfected plants, and that the regions of gene activity were no longer restricted to the elongation zone of the root. For example, in each location where a nematode was able to establish a feeding site, gene expression continued at that site for as long as 25–30 days (i.e., the duration of the nematode life cycle). In addition, at least one of the deletion constructions (Δ0.3) exhibited a delay before expression was detected in infected plants. The delay was observed to be 3–6 days after inoculation of the plant with nematodes.

EXAMPLE 5

Recombinant Nematode-Resistant Tobacco

This example is carried out in essentially the same manner as described in Examples 2 and 4 above, with the TobRB7 Δ0.3 deletion mutant (the nematode responsive element) as the promoter, and the gene encoding *Bacillus amyloliquefaciens* RNase (barnase), see C. Paddon and R. Hartley, *Gene* 40, 231–239 (1986), as the structural gene in the expression cassette. Barnase is known to be toxic to plant cells when expressed as a mature protein therein. See C. Mariani et al., *Nature* 347, 737–741 (1990).

Construction of the expression cassette containing the barnase gene is carried out in the plasmid pUC18 in *Escherichia coli* DH5α. The *E. coli* is protected from barnase during construction of the cassette essentially as described in R. Hartley, *J. Molec. Biol.* 202, 913–915 (1988). In brief, the bacteria is modified to include a second plasmid, pSa4, which has a different origin of replication from pUC18 and which expresses Barstar, with the Barstar binding to the Barnase to prevent the Barnase from digesting *E. coli* RNA.

The gene encoding the mature barnase protein (i.e., without the secretory leader sequence) is prepared in the following manner. A 5' synthetic oligonucleotide Barnase PCR primer is produced having, in the 5' to 3' order, a Bam HI restriction site, an initiating ATG codon, and 18 bases homologous to the N-terminus of the mature Barnase. A 3' synthetic oligonucleotide Barnase PCR primer is produced having, in the 5' to 3' order, 21 bases homologous to the C-terminus of the mature Barnase and a Sac I restriction site. PCR amplification of the Barnase gene with these two PCR primers produces a DNA sequence having, in the 5' to 3' order, a Bam HI restriction site, an initiating ATG codon, the entire coding sequence of the mature Barnase protein, and a Sac I restriction site. The Barnase gene so prepared is then spliced to the 3' end of the TobRB7 Δ0.3 promoter and this sequence is spliced to the 5' end of the termination sequence of the nos gene (the nos terminator).

The cassette (TobRB7 Δ0.3 promoter; ATG; mature Barnase coding sequence; nos terminator) produced above is cloned into the Agrobacterium binary vector pBin19 in *Agrobacterium tumefaciens* LBA4404, plant leaf discs transformed therewith, and whole plants regenerated as described in Example 2 above.

When tobacco plants carrying the foregoing cassette are infected with tobacco root-knot nematodes in the manner described in Example 4 above, the formation of giant cells is found to be hindered, and the life cycle of the nematodes is found to be adversely affected.

The foregoing examples are illustrative of the present invention, and are not to be construed as limiting thereof. The invention is defined by the following claims, with equivalents of the claims to be included therein.

That which is claimed is:

1. A recombinant nematode-resistant plant comprising transformed plant cells, said transformed plant cells containing a heterologous DNA construct comprising an expression cassette, which construct comprises, in the 5' to 3' direction, a promoter, a structural gene positioned downstream from said promoter and operatively associated therewith, and a termination sequence positioned downstream from said structural gene and operatively associated therewith, wherein said structural gene encodes a product toxic to said plant cells and wherein said promoter is a plant nematode-inducible promoter comprising a nucleotide sequence selected from:
   (a) SEQ ID NO:10; and
   (b) DNA sequences which have at least 60% sequences similarly to SEQ ID NO:10 and which are plant nematode-inducible promoters.

2. A recombinant plant according to claim 1, which promoter is activated by a nematode selected from the group consisting of root-knot nematodes and cyst nematodes.

3. A recombinant plant according to claim 1, wherein said resistance is to a nematode which attacks a tissue of said plant selected from the group consisting of leaf tissue and root tissue.

4. A recombinant plant according to claim 1, wherein said resistance is to a nematode which attacks the root tissue of said plant.

5. A recombinant plant according to claim 1, which plant is a monocot.

6. A recombinant plant according to claim 1, which plant is a dicot.

7. A recombinant plant according to claim 1, which plant is a dicot selected from the group consisting of tobacco, potato, soybean, peanuts, pineapple, cotton, and vegetable crops.

8. A recombinant plant according to claim 1, which structural gene encodes an enzyme capable of digesting a nucleic acid selected from the group consisting of DNA and RNA.

9. A recombinant plant according to claim 1, which structural gene encodes *Bacillus amyloliquefaciens* RNase.

10. A recombinant nematode-resistant plant comprising:

transformed dicotyledonous plant cells, said transformed dicotyledonous plant cells containing a heterologous DNA construct comprising an expression cassette, which construct comprises, in the 5' to 3' direction, a promoter, a structural gene positioned downstream from said promoter and operatively associated therewith, and a termination sequence downstream from said structural gene and operatively associated therewith, wherein said promoter is a plant nematode-inducible promoter comprising a nucleotide sequence selected from:
(a) SEQ ID NO:10; and
(b) DNA sequences which have at least 60% sequences similarity to SEQ ID NO:10 and which are plant nematode-inducible promoters, and wherein said structural gene encodes a product toxic to said plant cells.

11. A recombinant plant according to claim 10, which promoter is activated by a nematode selected from the group consisting of root-knot nematodes and cyst nematodes.

12. A recombinant plant according to claim 10, which plant is a dicot selected from the group consisting of tobacco, potato, soybean, peanuts, pineapple, cotton, and vegetable crops.

13. A recombinant plant according to claim 10, which structural gene encodes an enzyme capable of digesting a nucleic acid selected from the group consisting of DNA and RNA.

14. A recombinant plant according to claim 10, which structural gene encodes *Bacillus amyloliquefaciens* RNase.

15. A crop comprising a plurality of plants according to claims 1 or 10 planted together in an agricultural field.

16. A method of combatting nematodes in an agricultural field, comprising planting the field with a crop of recombinant nematode-resistant plants comprising transformed plant cells, said transformed plant cells containing a heterologous DNA construct comprising an expression cassette, which construct comprises, in the 5' to 3' direction, a promoter, a structural gene positioned downstream from said promoter and operatively associated therewith, and a termination sequence positioned downstream from said structural gene and operatively associated therewith, wherein said structural gene encodes a product toxic to said plant cells, and wherein said promoter is a plant nematode-inducible promoter comprising a nucleotide sequence selected from:
(a) SEQ ID NO:10; and
(b) DNA sequences which have at least 60% similarity to SEQ ID NO:10 and which are plant nematode-inducible promoters.

17. A method of making a recombinant nematode-resistant plant, said method comprising;

providing a plant cell capable of regeneration;

transforming said plant cell with a DNA construct comprising an expression cassette, which construct comprises, in the 5' to 3' direction, a promoter, a structural gene positioned downstream from said promoter and operatively associated therewith, and a termination sequence positioned downstream from said structural gene and operatively associated therewith, said structural gene encoding a product toxic to plant cells, and said promoter being a plant nematode-inducible promoter comprising a nucleotide sequence selected from:

(a) SEQ ID NO:10; and
(b) DNA sequences which have at least 60% sequence similarity to SEQ ID NO:10 and which are plant nematode-inducible promoters;

and then regenerating a recombinant pathogen-resistant plant from said transformed plant cell.

18. A method according to claim 17, wherein said plant cell resides in a plant tissue capable of regeneration.

19. A method according to claim 17, wherein said transforming step is carried out by bombarding said plant cell with microparticles carrying said expression cassette.

20. A method according to claim 17, wherein said transforming step is carried out by infecting said cells with an *Agrobacterium tumefaciens* containing a Ti plasmid carrying said expression cassette.

21. A DNA construct comprising an expression cassette, which construct comprises, in the 5' to 3' direction, a promoter, a structural gene positioned downstream from said promoter and operatively associated therewith, and a termination sequence positioned downstream from said structural gene and operatively associated therewith, said structural gene encoding a product toxic to plant cells, and said promoter being a plant nematode-inducible promoter comprising a nucleotide sequence selected from:

(a) SEQ ID NO:10; and
(b) DNA sequences which have at least 60% sequence similarity to SEQ ID NO:10 and which are plant nematode-inducible promoters.

22. A DNA construct according to claim 21 carried by a plant transformation vector.

23. A recombinant nematode-resistant plant comprising transformed plant cells, said transformed plant cells containing a heterologous DNA construct, which construct comprises, in the 5' to 3' direction, a promoter, a structural gene positioned downstream from said promoter and operatively associated therewith, and a termination sequence positioned downstream from said structural gene and operatively associated therewith, wherein said structural gene encodes a product toxic to said plant cells;

and wherein said promoter is a plant nematode inducible promoter comprising SEQ ID NO:10.

24. A recombinant plant according to claim 23, which plant is a monocot.

25. A recombinant plant according to claim 23, which plant is a dicot.

26. A recombinant plant according to claim 23, which plant is a dicot selected from the group consisting of tobacco, potato, tomato, soybean, rice, and cotton.

27. A recombinant plant according to claim 23, which structural gene encodes an enzyme capable of digesting a nucleic acid selected from the group consisting of DNA and RNA.

28. A recombinant plant according to claim 23, which structural gene encodes *Bacillus amyloliquefaciens* RNase.

29. A recombinant pathogen-resistant tobacco plant comprising transformed tobacco plant cells, said transformed tobacco plant cells containing a heterologous DNA construct, which construct comprises, in the 5' to 3' direction, a nematode-inducible promoter, a structural gene positioned downstream from said nematode-inducible promoter operatively associated therewith, and a termination sequence positioned downstream from said structural gene and operatively associated therewith, wherein said structural gene encodes a product toxic to said tobacco plant cells so that activation of said nematode-inducible promoter in a cell of said tobacco plant causes the death of that cell;

and wherein said nematode-inducible promoter is Δ0.3 TobRB7 of SEQ ID NO:10.

30. A recombinant tobacco plant according to claim 29, which structural gene encodes an enzyme capable of digesting a nucleic acid selected from the group consisting of DNA and RNA.

31. A recombinant tobacco plant according to claim 29, which structural gene encodes *Bacillus amyloliquefaciens* RNase.

32. A recombinant nematode-resistant plant of the family Solanaceae, wherein cells of said plant are transformed to contain a heterologous DNA construct, which construct comprises, in the 5' to 3' direction, a promoter, a structural gene positioned downstream from said promoter and operatively associated therewith, and a termination sequence positioned downstream from said structural gene and operatively associated therewith, wherein said structural gene encodes a product toxic to cells of said plant so that activation of said nematode-inducible promoter in a cell of said plant causes the death of that cell; and wherein said promoter is a plant nematode inducible promoter comprising a nucleotide sequence selected from;
   (a) SEQ ID NO:10; and
   (b) DNA sequences which have at least 60% sequence identity to SEQ ID NO:1 and which are plant nematode-inducible promoters.

33. A recombinant plant according to claim 32, where said nematode-inducible promoter has the sequence of SEQ ID NO:10.

34. A recombinant plant according to claim 32, which plant is selected from the group consisting of tobacco, potato, and tomato.

35. A recombinant plant according to claim 32, which structural gene encodes an enzyme capable of digesting a nucleic acid selected from the group consisting of DNA and RNA.

36. A recombinant plant according to claim 32, which structural gene encodes *Bacillus amyloliquefaciens* RNAse.

37. A recombinant plant according to claim 23, which plant is a member of the family Solanaceae.

38. A method according to claim 17, wherein said promoter is activated by a nematode selected from the group consisting of root-knot nematodes and cyst nematodes.

39. A method according to claim 17, wherein said recombinant nematode resistant plant is a dicot.

40. A method according to claim 17, wherein said recombinant nematode resistant plant is a plant of the family Solanaceae.

41. A method according to claim 17, wherein said recombinant nematode resistant plant is a dicot selected from the group consisting of tobacco, potato, soybean, peanuts, pineapple, cotton, and vegetable crops.

42. A method according to claim 17, wherein said structural gene encodes an enzyme capable of digesting a nucleic acid selected from the group consisting of DNA and RNA.

43. A method according to claim 17, wherein said structural gene encodes *Bacillus amyloliquefaciens* RNase.

44. A method according to claim 16, wherein said crop consists of recombinant nematode-resistant Solanaceae plants, and said promoter comprises SEQ ID NO:10.

45. A method according to claim 44, wherein said structural gene encodes an enzyme capable of digesting a nucleic acid selected from the group consisting of DNA and RNA.

46. A method according to claim 44, wherein said structural gene encodes *Bacillus amyloliquefaciens* RNase.

* * * * *

UNITED STATES PATENT AND TRADEMARK OFFICE
CERTIFICATE OF CORRECTION

PATENT NO. : 5,750,386
DATED : 12 May 1998
INVENTOR(S) : Mark A. Conkling, Charles H. Opperman, Christopher G. Taylor It is certified that error appears in the above-identified patent and that said Letters Patent is hereby corrected as shown below:

Column 1, line 6, please replace "07/770,002" with -- 07/770,082--.

Column 11, line 57, please replace "15A" to --λ5A --.

In claim 1, line 14-15, please replace "sequences similarly" to -- sequence similarity --.

In claim 1, line 16, please replace "nematode-inductible" to -- nematode-inducible --.

Signed and Sealed this

Fifteenth Day of June, 1999

*Attest:*

Q. TODD DICKINSON

*Attesting Officer*     *Acting Commissioner of Patents and Trademarks*